US006218377B1

(12) United States Patent
Stogniew et al.

(10) Patent No.: US 6,218,377 B1
(45) Date of Patent: *Apr. 17, 2001

(54) METHODS FOR THE ADMINISTRATION OF AMIFOSTINE AND RELATED COMPOUNDS

(75) Inventors: Martin Stogniew, Blue Bell; Philip S. Schein, Bryn Mawr, both of PA (US)

(73) Assignee: MedImmune Oncology Inc., West Conshohocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/586,753

(22) Filed: Jun. 5, 2000

Related U.S. Application Data

(63) Continuation of application No. 09/021,139, filed on Feb. 10, 1998, now Pat. No. 6,127,351, which is a continuation-in-part of application No. 08/798,840, filed on Feb. 12, 1997, now Pat. No. 6,051,563.

(51) Int. Cl.[7] .................................................. A01N 57/00
(52) U.S. Cl. .......................................... 514/114; 558/146
(58) Field of Search .............................. 514/114; 558/146

(56) References Cited

U.S. PATENT DOCUMENTS

| | | | |
|---|---|---|---|
| 3,892,824 | * 7/1975 | Piper et al. | 558/166 |
| 5,424,471 | * 6/1995 | Kennedy et al. | 558/146 |
| 5,466,678 | * 11/1995 | Kawabata et al. | 514/46 |
| 5,591,731 | 1/1997 | Kennedy et al. | 514/114 |
| 5,807,744 | * 9/1998 | Berneman et al. | 435/372 |
| 5,846,958 | * 12/1998 | Capizzi et al. | 514/114 |
| 6,051,563 | * 4/2000 | Stogniew et al. | 514/114 |
| 6,127,351 | * 10/2000 | Stogniew et al. | 514/114 |

OTHER PUBLICATIONS

Berkow et al. (eds.), "Myelodysplastic Syndrome," in Ch. 99 of *The Merck Manual of Diagnosis and Therapy*, 16th Ed., Merck & Co., Inc., Rahway, NJ, May, 1992, pp. 1243–1245.*

Betticher et al., 1995, "Carboplatin combined with amifostine, a bone marrow protectant, in the treatment of non-small-cell lung cancer: a randomised phase II study," *Br. J. Cancer 5*: 1551–1555 Month of publication data is unavailable for this reference.

Büntzel et al., 1996, "Ethyol® (Amifostine) Provides Multilineage Hematoprotection and Protection Against Non–Hematologic Toxicities Induced by Radiochemotherapy (RCT) of Head and Neck Cancer," *Blood 88*(Suppl. 1):1781 Month of publication data is unavailable for this reference.

Büntzel et al., 1996, "Selective Cytoprotection with Amifostine in Simultaneous Radiochemotherapy of Head Neck Cancer," *Annals of Oncology 7*(Suppl. 5):81(381P) Month of publication data is unavailable for this reference.

Constine et al., 1986, "Protection by WR–2721 of Human Bone Marrow Function Following Irradiation," *Int. J. Radiation Oncology Biol. Phys. 12*:1505–1508 Month of publication data is unavailable for this reference.

DiPaola et al., 1996, "A Phase I Study of Amifostine and Paclitaxel with Advanced Malignancies," *Proceedings of ASCO 15*:488(1156) Month of publication data is unavailable for this reference.

Dorr et al., 1995, "Selective Cardioprotection of Rat Heart Myocytes Exposed to DNA Intercalating Agents Using Amifostine (AMI) and its Dephosphorylated Metabolite, WR–1065," *Eur. J. Cancer 31A*(Suppl. 5):S123(579) Month of publication data is unavailable for this reference.

Glover et al., 1986, "WR–2721 Protects Against the Hematologic Toxicity of Cyclophosphamide: A Controlled Phase II Trial," *J. Clin. Oncol. 4*:584–588 Month of publication data is unavailable for this reference.

Goodman et al., *The Pharmacological Basis of Theapeutics*, 8th Edition, Pergamon Press, New York, NY, 1990, only Title pages and text pp. 5–9 supplied, Month of publication data is unavailable for this reference.

Kemp et al. 1996, "Amifostine Pretreatment for Protection Against Cyclophosphamide–Induced and Cisplatin–Induced Toxicities: Results of a Randomized Control Trial in Patients with Advanced Ovarian Cancer," *J. Clin. Oncol. 14*:2101–2112 Month of publication data is unavailable for this reference.

List et al., 1996, "Amifostine Protects Primitive Hematopoietic Progenitors Against Chemotherapy Cytotoxicity," *Seminars in Oncology 23*(4)Suppl. 8–58–63 Month of publication data is unavailable for this reference.

List et al., 1996, Amifostine Promotes Multilineage Hematopoiesis in Patients with Myelodysplastic Syndrome (MDS): Results of a Phase I/II Clinical Trial, *Blood 88*(10) Suppl 1:453a(1802) (abstract) Month of publication data is unavailable for this reference.

List et al., 1996, "Amifostine Stimulates Formation of Multipotent Progenitors and Generates Macroscopic Colonies in Normal and Myelodysplastic Bone Marrow," *Proceedings of ASCO 15*:449(1403) Month of publication data is unavailable for this reference.

Liu et al., 1992, "Use of Radiation With of Without WR–2721 in Advanced Rectal Cancer," *Cancer 69*:2820–2825 Month of publication data is unavailable for this reference.

(List continued on next page.)

*Primary Examiner*—Gary Geist
*Assistant Examiner*—L. E. Crane
(74) *Attorney, Agent, or Firm*—Pennie & Edmonds LLP

(57) ABSTRACT

The present invention provides methods of administering aminoalkyl phosphorothioate and/or aminoalkyl thiol compounds to patients in a manner that significantly reduces or decreases the adverse or undesirable side-effects of the compounds as compared with conventional intravenous administration.

22 Claims, 10 Drawing Sheets

OTHER PUBLICATIONS

McDonald et al., 1994, "Preliminary Results of a Pilot Study Using WR–2721 Before Fractionated Irradiation of the Head and Neck to Reduce Salivary Gland Dysfunction," *Int. J. Radiation Oncology Biol. Phys. 29*:747–754 Month of publication data is unavailable for this reference.

McDonald et al., 1995, "Amifostine Preserves the Salivary Gland Function During Irradiation of the Head and Neck," *European Journal of Cancer 31A*(Suppl. 5):415 Month of publication data is unavailable for this reference.

Nema S, et al., "Excipients and their use in injectable products", PDA J Pharm Sci Technol. 1997 Jul.–Aug.;51(4):166–71 Month of publication data is unavailable for this reference.

Phillips and Wasserman, 1984, "Promise of Radiosensitizers and Radioprotectors in the Treatment of Human Cancer," *Cancer Treat. Rep. 68*:291–302 Month of publication data is unavailable for this reference.

Reiger, M.M., 1996, *Surfactant Encyclopedia*, 2$^{nd}$ Edition, pp. 17–18, Month of publication data is unavailable for this reference.

Schiller et al., 1996, "Amifostine, Cisplatin, and Vinblastine in Metastatic Non–Small–Cell Lung Cancer: A Report of High Response Rates and Prolonged Survival," *J. Clin. Oncol. 14*(6):1913–1921 Month of publication data is unavailable for this reference.

Shaw et al., 1994, "Pharmacokinetics of Amifostine in Cancer Patients: Evidence for Saturable Metabolism," *Proceedings of ASCO 13*:144(371) Month of publication data is unavailable for this reference.

Shaw et al., 1988, "Pharmacokinetics of WR–2721," *Pharmac. Ther. 39*:195–201 Month of publication data is unavailable for this reference.

Shaw et al., 1986, "Human Pharmacokinetics of WR–2721," *Int. J. Radiation Oncology Biol. Phys. 12*:1505–1504 Month of publication data is unavailable for this reference.

Tabachnik et al., 1980, "Studies on the Reduction of Sputum Viscosity in Cystic Fibrosis Using an Orally Absorbed Protected Thiol," *J. Pharmacol. Exp. Ther. 214*:246–249 Month of publication data is unavailable for this reference.

Tabachnik et al., 1982, "Protein Binding of N–2–Mercaptoethyl–1,3–Diaminopropane via Mixed Disulfide Formation after Oral Administration of WR 2721," *J. Pharmacol. Exp. Ther. 220*:243–246 Month of publication data is unavailable for this reference.

Trissel LA, et al., "Compatibility of amifostine with selected drugs during simulated Y–site administration", Am J Health Syst Pharm. Oct. 15, 1995;52(20):2208–12, Month of publication data is unavailable for this reference.

Wadler et al., 1993, "Pilot Trial of Cisplatin, Radiation, and WR2721 in Carcinoma of the Uterine Cervix: A New York Gynecologic Oncology Group Study," *J. Clin. Oncol. 11*:1511–1516 Month of publication data is unavailable for this reference.

Wasserman et al., 1981, "Differential protection against cytotoxic chemotherapeutic effects on bone marrow CFUs by WR–2721," *Cancer Clin. Trials 4*:3–6 Month of publication data is unavailable for this reference.

Yuhas, 1973, "Radiotherapy of Experimenting Lung Tumors in the Presence and Absence of a Radioprotective Drug, S–2–(3–aminopropylamino)ethylphosphorothioic Acid (WR–2721)," *J. Natl. Cancer. Inst. 50*:69–78 Month of publication data is unavailable for this reference.

* cited by examiner

METHODS FOR THE ADMINISTRATION OF AMIFOSTINE AND RELATED COMPOUNDS

CROSS REFERENCE TO RELATED APPLICATIONS

The present application is a continuation of application Ser. No. 09/021,139, filed Feb. 10, 1998, now U.S. Pat. No. 6,127,351, which is a continuation-in-part of application Ser. No. 08/798,840, filed Feb. 12, 1997, now U.S. Pat. No. 6,051,563, issued Apr. 18, 2000.

INTRODUCTION

The present invention relates to methods of administering aminoalkyl phosphorothioate and/or aminoalkyl thiol compounds to a subject in a manner that reduces or decreases the undesirable side effects of the compounds. One aspect of the invention relates to the subcutaneous administration of amifostine and/or its active metabolite to a patient, which reduces adverse side effects. Another aspect of the invention relates to methods of administering amifostine and/or its active metabolite to a patient in a manner such that a characteristic pharmacokinetic profile is obtained. When administered according to the characteristic pharmacokinetic profile, fewer adverse side effects are experienced by patients.

BACKGROUND OF THE INVENTION

Amifostine (also known as WR-2721) has been shown to be useful as a radiation protectant in cancer patients receiving radiation therapy (Constine et al., 1986, "Protection by WR-2721 of Human Bone Marrow Function Following Irradiation" *Int. J. Radia. Oncol. Biol. Phys.* 12:1505–8; Liu et al., 1992, "Use of Radiation with or Without WR-2721 in Advanced Rectal Cancer" *Cancer* 69(11):2820–5; Wadler et al., 1993, "Pilot Trial of Cisplatin, Radiation and WR-2721 in Carcinoma of the Uterine Cervix: A New York Gynecologic Oncology Group Study" *J. Clin. Oncol.* 11(8):1511–6; Buntzel et al., 1996, "Selective Cytoprotection with Amifostine in Simultaneous Radiochemotherapy of Head Neck Cancer" *Ann. Oncol.* 7(Suppl.5):81(381P)). Amifostine is a pro-drug that is dephosphorylated at the tissue site by alkaline phosphatase to the free thiol, which is the active metabolite (also known as WR-1065). Once inside the cell, the active free thiol can protect against the toxicities associated with radiation by acting as a scavenger for oxygen free-radicals that are produced by ionizing radiation (Yuhas, 1977, "On the Potential Application of Radioprotective Drugs in Solid Tumor Radiotherapy," *In: Radiation-Drug Interactions in Cancer Management* pp. 303–52; Yuhas, 1973, "Radiotherapy of Experimental Lung Tumors in the Presence and Absence of a Radioprotective Drug S-2-(3-Aminopropylamino) thylphosphorothioc Acid (WR-2721)" *J. Natl. Cancer Inst.* 50:69–78; Philips et al., 1984, "Promise of Radiosensitizers and Radioprotectors in the Treatment of Human Cancer" *Cancer Treat. Rep.* 68:291–302).

Amifostine's ability to selectively protect normal tissues is based on the differential metabolism and uptake of amifostine into normal tissue versus tumor tissue. Amifostine is rapidly taken up and retained in normal tissues. Differences in capillary and membrane-bound alkaline phosphatase concentration and pH between normal and tumor tissues have been shown to favor the conversion of the pro-drug and uptake of the active form of amifostine, the free thiol, into normal tissues. Coupled with the fact that normal cells concentrate the free thiol at a faster rate than tumors and retain it for longer periods of time, amifostine is able to selectively protect normal tissues against the toxicities associated with radiation without negatively affecting the anti-tumor response. The marked differences in tissue uptake and retention between normal and tumor tissues produces a temporary state of acquired drug resistance in normal tissues, analogous to that produced by an excess of endogenous glutathione.

For a cytoprotector to be useful in radiation therapy, the compound must be tolerated on a daily basis, up to 4 or 5 days a week for several weeks, prior to the delivery of conventional doses of radiation. McDonald et al. (McDonald, 1994, "Preliminary Results of a Pilot Study Using WR-2721 Before Fractionated Irradiation of Head and Neck to Reduce Salivary Gland Dysfunction" *Int. J. Radiat. Oncol. Biol. Phys.* 29(4):747–54; McDonald et al., 1995, "Amifostine Preserves the Salivary Gland Function During Irradiation of the Head and Neck" *Eur. J. Cancer* 31a (Supp. 5):415) have conducted a dose-escalation study of amifostine and radiation in patients with head and neck cancer. These results suggest that daily administration of amifostine (200 mg/$M^2$ via a 6-minute intravenous infusion) prior to radiation protects the salivary gland against the toxicities of radiation.

Amifostine has also been shown to stimulate bone marrow growth, and is currently in Phase II clinical trials as a bone marrow stimulant in patients suffering from myelodysplastic syndrome (List et al., 1996, "Amifostine Promotes Multilineage Hematopoiesis in Patients with Myelodysplastic Syndrome (MDS): Results of a Phase I/II Clinical Trial" *Am. J. Hem.* 1 (Abstract); List et al., 1996, "Amifostine Promotes in vitro and in vivo Hematopoiesis in Myelodysplastic Syndromes" *Chem. Found Sympos.* (Abstract); List et al., 1996, "Amifostine Promotes Multilineage Hematopoiesis in Patients with Myelodysplastic Syndrome (MDS): Results of a Phase I/II Clinical Trial," Abstract, 8th Annual Meeting, American Society of Hematology, Orlando, FL). In this study, amifostine is being administered via intravenous infusion.

Intravenous administration of amifostine suffers from several serious drawbacks. First, administering compounds intravenously is extremely inconvenient, particularly when a daily dosing schedule for several weeks, or potentially several months in the case of MDS, is necessary, requiring a skilled practitioner to administer the dose. Second, when administered intravenously, patients suffer from dose-dependent undesirable side-effects such as nausea, vomiting, emesis and hypotension, as well as flushing or feeling of warmth, chills or feeling of coldness, dizziness, somnolence, hiccups and sneezing. A decrease in serum calcium concentration is a known pharmacological effect of intravenously administered amifostine. Allergic reactions ranging from mild skin rashes to rigors have also rarely occurred in conjunction with intravenously administered amifostine. At present, there are no known methods, other than co-administering agents such as anti-emetics, of reducing or avoiding these undesirable side effects. Third, there are related costs associated with intravenous administration, including personnel, equipment and medical measures to attenuate side effects.

The human pharmacokinetic profile of amifostine has been investigated in cancer patients following a single intravenous bolus dose (150 mg/kg) (Shaw et al., 1986, "Human Pharmacokinetics of WR-2721" *Int. J. Radiat. Oncol. Biol. Phys.* 12:1501–4), a single 15-minute intravenous infusion (up to 910 mg/$m^2$) (Shaw et al., 1988, "Pharmacokinetics of WR-2721" *Pharmac. Ther.* 39:195–201; Shaw et al., 1994, "Pharmacokinetics of Amifostine in Cancer Patients: Evidence for Saturable Metabolism" *Proc. Amer. Cos. Clin. Oncol.* 13:144; U.S. Bioscience, 1994, "Pharmacokinetics of Single Dose Amifostine (WR-2721; Ethyol)" ETH PK 3) and repeated infusions (up to 910 mg/m$^2$ per dose) (U.S. Bioscience, 1994, "Pharmacokinetics of Double Dose Amifostine (WR-2721; Ethyol) with Corresponding Measurements of WR-1065 in Plasma and Bone Marrow Cells" ETH PK 4). These studies showed that amifostine is rapidly cleared from the plasma with a distribution half-life of less than 1 minute and an elimination half-life of approximately 9 minutes. Less than 10% of amifostine remained in the plasma 6 minutes after intravenous administration. No previous human clinical pharmacokinetic studies have been conducted using either orally or subcutaneously administered amifostine.

Tabachnik reported that the oral administration of amifostine reduced sputum viscosity in cystic fibrosis patients (Tabachnik et al., 1980, "Studies on the Reduction of Sputum Viscosity in Cystic Fibrosis Using an Orally Absorbed Protected Thiol." *J. Pharm. Exp. Ther.* 214:246–9; Tabachnik et al., 1982, "Protein Binding of N-2-Mercaptoethyl-1 3-Diaminopropane via Mixed Disulfide Formation After Oral Administration of WR-2721" *J. Pharm Exp. Ther.* 220:243–6). However, these studies did not demonstrate that this mode of administration reduced adverse side effects commonly associated with intravenously administered amifostine. Furthermore, a study of the pharmacokinetic profile of the admnistered compounds was not conducted in these patients.

SUMMARY OF THE INVENTION

The present invention provides methods of administering aminoalkyl phosphorothioate and/or aminoalkyl thiol compounds to a subject, including humans, in a manner which decreases or reduces the undesirable side effects of the compounds. One aspect of the invention relates to the subcutaneous administration of an aminoalkyl phosphorothioate and/or aminoalkyl thiol compound to a human subject. Another aspect of the invention relates to the administration of an aminoalkyl phosphorothioate and/or aminoalkyl thiol compound to a patient in a manner such that a characteristic pharmacokinetic profile is obtained. The pharmacokinetic profile is generally characterized by a first region wherein the plasma and/or a whole blood concentration of administered compound, an active metabolite thereof, or both gradually increases to a maximum concentration, a second region wherein the maximum plasma and/or whole blood concentration is substantially maintained, or plateaus, and a third region wherein the plasma and/or whole blood concentration gradually decreases to baseline levels. The rate at which the plasma and/or whole blood concentration of the administered compound (and/or an active metabolite thereof) increases to the maximum level is markedly slower than that achieved with conventional intravenous administration.

Administering aminoalkyl phosphorothioate and/or aminoalkyl thiol compounds according to the methods of the invention significantly reduces or decreases the adverse or undesirable side effects suffered by patients as compared to conventional intravenous administration, without substantially affecting the efficacy of the applied dose. Thus, the methods of the invention can be advantageously used in conjunction with treatment strategies for delivering aminoalkyl phosphorothioate and/or aminoalkyl thiol compounds to patients without inducing the vomiting, nausea, emesis, hypotension or other undesirable side-effects, including but not limited to, flushing or feeling of warmth, chills or feeling of coldness, dizziness, somnolence, hiccups, sneezing, decreased serum calcium levels and allergic reactions that are commonly experienced with conventional intravenous administration.

BRIEF DESCRIPTION OF THE DRAWINGS

FIG. 7A shows the formation of CFU-GEMM colonies, FIG. 7B shows the formation of BFU-E colonies and FIG. 7C shows the formation of CFU-GM colonies.

DETAILED DESCRIPTION OF THE INVENTION

Figure 1:
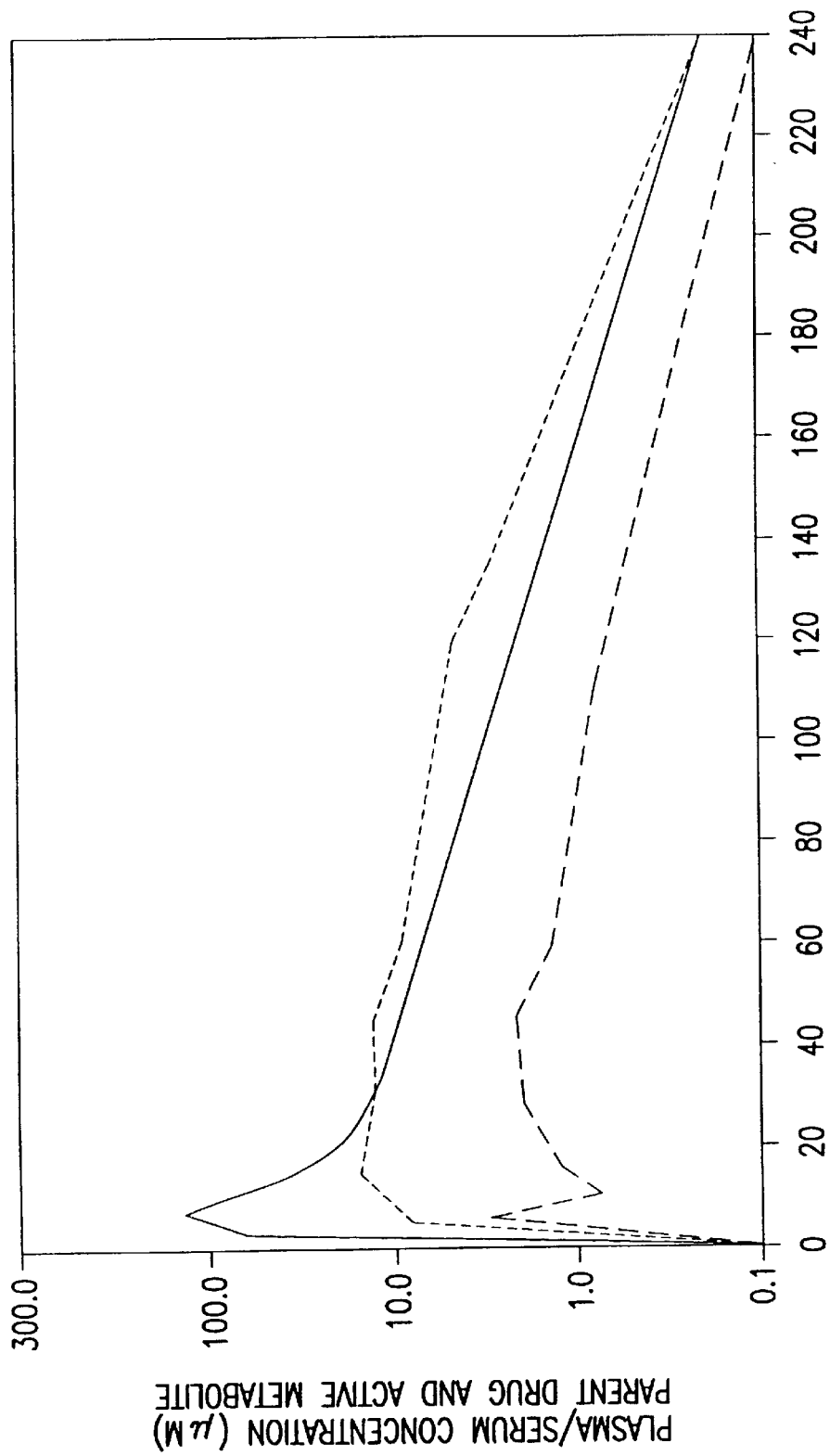
FIG. 1 is a graph of the average whole blood concentration-time curves for amifostine (parent drug WR-2721 plus active metabolite WR-1065) following a 500 mg subcutaneous injection, a 500 mg oral solution and a 200 mg/m$^2$ intravenous infusion (over 7.5 minutes) to 12 subjects, 0 to 240 minutes after drug administration (—— iv; --- sc; —— —— oral).

The present invention provides methods of administering aminoalkyl phosphorothioate and/or aminoalkyl thiol compounds to patients in a manner which decreases the undesirable side effects of the compounds as compared to conventional intravenous administration. The invention is based, in part, on the quite unexpected discovery that human patients receiving subcutaneously administered amifostine experienced significantly fewer incidences of nausea, vomiting, headache, hypotension, lightheadness, somnolence and other undesirable side effects commonly associated with conventional intravenous administration of amifostine than did patients who received amifostine via conventional intravenous infusion. These side effects coincide with the "spike" or "burst" phase of the pharmacokinetic profile of intravenously administered drug.

The invention is further based, in part, on the observation that the pharmacokinetic profiles of amifostine and its active metabolite WR-1065 for intravenously and subcutaneously administered amifostine are significantly different. Whereas whole blood concentrations of both amifostine and its active metabolite WR-1065 peaked and declined rapidly within the first 10 minutes following intravenous administration of amifostine, whole blood concentrations of both of these compounds increased at a markedly slower rate following subcutaneous amifostine administration, reaching maximum and sustained concentration about 15–45 minutes after administration.

While not intending to be bound by theory, it is believed that the decrease in undesirable side effects observed for subcutaneously administered amifostine as compared to intravenously administered amifostine is in part due to the characteristic pharmacokinetic profile associated with subcutaneous administration. Thus, in the methods of the invention a therapeutically effective amount of an aminoalkyl phosphorothioate and/or aminoalkyl thiol compound is administered to a patient in a manner such that a characteristic pharmacokinetic profile for either the administered compound and/or an active metabolite thereof is obtained, thereby significantly reducing the undesirable side effects suffered by patients receiving such therapy as compared with conventional intravenous administration.

The Compounds

Compounds which can be advantageously administered according to the methods described herein are aminoalkyl phosphorothioate or aminoalkyl thiol compounds which exhibit selective radioprotection or chemoprotection of normal tissues, and/or bone marrow stimulating or healing activities, and which are suitable for human use with minimal toxicity. Such aminoalkyl phosphorothioate or aminoalkyl thiol compounds, as well as pharmaceutically acceptable addition salts and/or hydrates thereof, are either known to those of skill in the art or can be identified without undue experimentation using established tests routinely employed in the art.

In one illustrative embodiment, compounds that can be advantageously administered via the methods of the invention are compounds having the formula:

$$R_1NH(CH_2)_nNH(CH_2)_mSR_2 \quad (I)$$

or pharmaceutically acceptable addition salts or hydrates thereof, wherein:

$R_1$ is hydrogen, $C_1$–$C_7$ aryl, $C_1$–$C_7$ acyl or $C_1$–$C_7$ alkyl;

$R_2$ is hydrogen or $PO_3H_2$;

n is an integer from 2 to 6; and m is an integer from 2 to 6.

All of the compounds of formula (I) may be prepared by methods known in the art (see, e.g., Cortese, 1943, *Organic Synthesis* pp. 91–93, Coll. Vol. II, Blatt, Ed., John Wiley & Sons, Inc., New York, NY; Akerfeldt, 1960, *Acta Chem. Scand.* 14:1980; Piper et al., 1966, *Chem. Ind.* (London): 2010). Certain aminoalkyl phosphorothioate compounds according to formula (I), as well as methods of synthesizing such compounds, are described in detail in U.S. Pat. No. 3,892,824 and WO 96/25045, each of which is incorporated herein by reference in its entirety.

The aminoalkyl phosphorothioate and/or aminoalkyl thiol compounds useful in the methods of the invention may be in the form of free acids, free bases, or pharmaceutically acceptable addition salts thereof. Such salts can be readily prepared by treating an aminoalkyl phosphorothioate or aminoalkyl thiol compound with an appropriate acid. Such acids include, by way of example and not limitation, inorganic acids such as hydrohalic acids (hydrochloric, hydrobromic, hydrofluoric, etc.), sulfuric acid, nitric acid, phosphoric acid, etc. and organic acids such as acetic acid, propanoic acid, 2-hydroxyacetic acid, 2-hydroxypropanoic acid, 2-oxopropanoic acid, propandioic acid, butandioic acid, etc. Conversely, the salt can be converted into the free base form by treatment with alkali.

The aminoalkyl phosphorothioate and/or aminoalkyl thiol compounds useful in the methods of the invention, as well as the pharmaceutically acceptable addition salts thereof, may be in a hydrated or unhydrated form. Methods of preparing such forms will be apparent to those of skill in the art of organic chemistry.

In a preferred embodiment of the invention, the compounds are those of formula (I), or pharmaceutically acceptable addition salts or hydrates thereof, wherein:

$R_1$ is hydrogen or methyl;

$R_2$ is hydrogen or $PO_3H_2$;

n is 3; and m is 2 or 3.

In a particularly preferred embodiment of the invention, the compound is S-2-(3-aminopropyl)ethyl dihydrogen phosphorothioate, $N_2H(CH_2)_3NH(CH_2)_2SPO_3H_2$ (amifostine or WR-2721), particularly the mono- and trihydrates thereof; 2-[3-aminopropylamino]ethanethiol, $N_2H(CH_2)_3NH(CH_2)_2SH$ (the active metabolite of amifostine or WR-1065); S-3-(3-methylaminopropylamino)propyl dihydrogen phosphorothioate, $CH_3NH(CH_2)_3NH(CH_2)_3SPO_3H_2$ (WR-151327); or S-3-(3-methylaminopropylamino propane thiol, $CH_3NH(CH_2)_3NH(CH_2)_3SH$ (WR-151326).

Pharmacokinetic Profile

Figure 2:
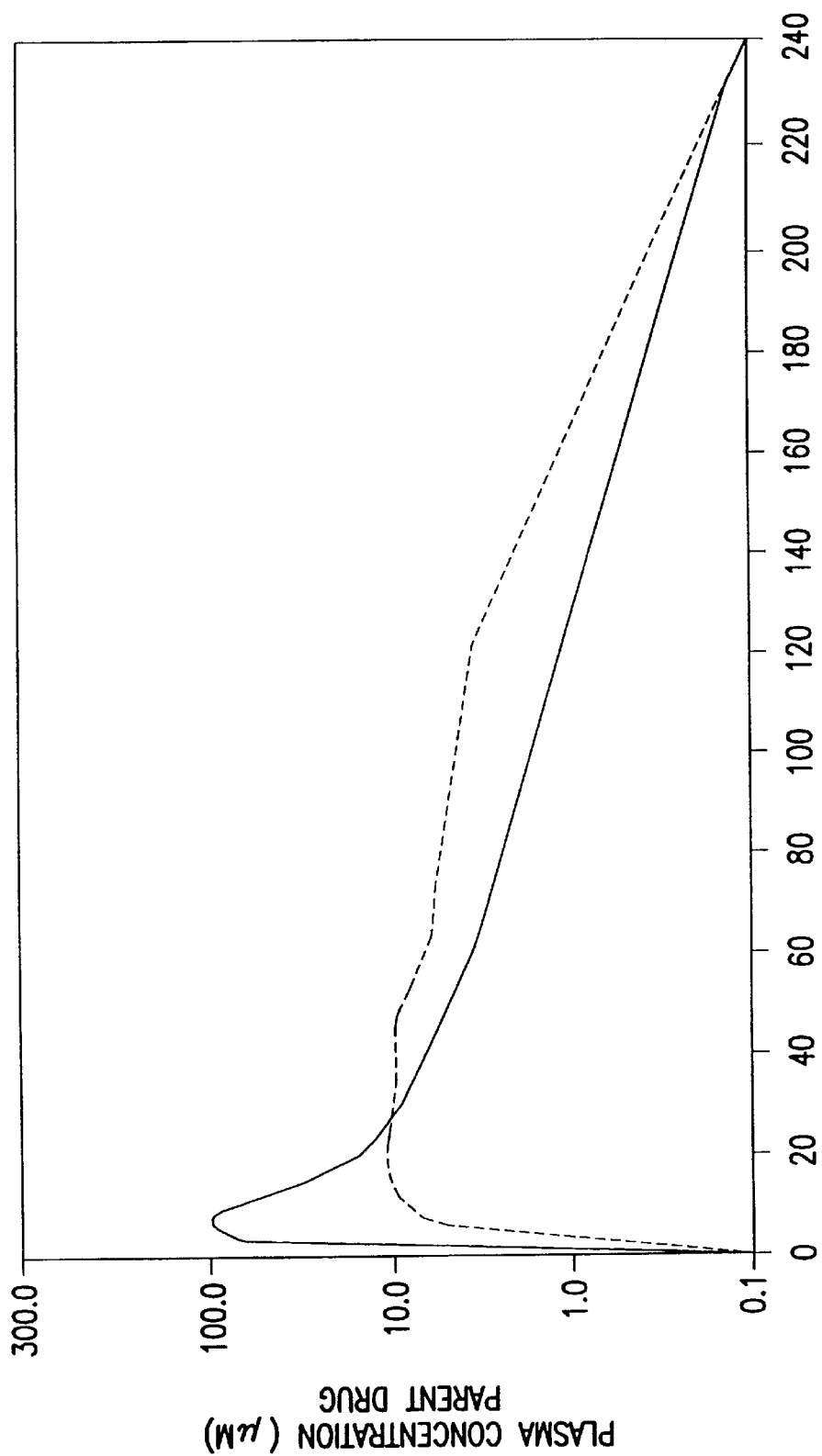
FIG. 2 is a graph of the average plasma concentration-time curves for amifostine (parent drug WR-2721) following a 500 mg subcutaneous injection, and a 200 mg/m$^2$ intravenous infusion (over 7.5 minutes) to 12 subjects, 0 to 240 minutes after drug administration (—— iv; --- sc).
Figure 3:
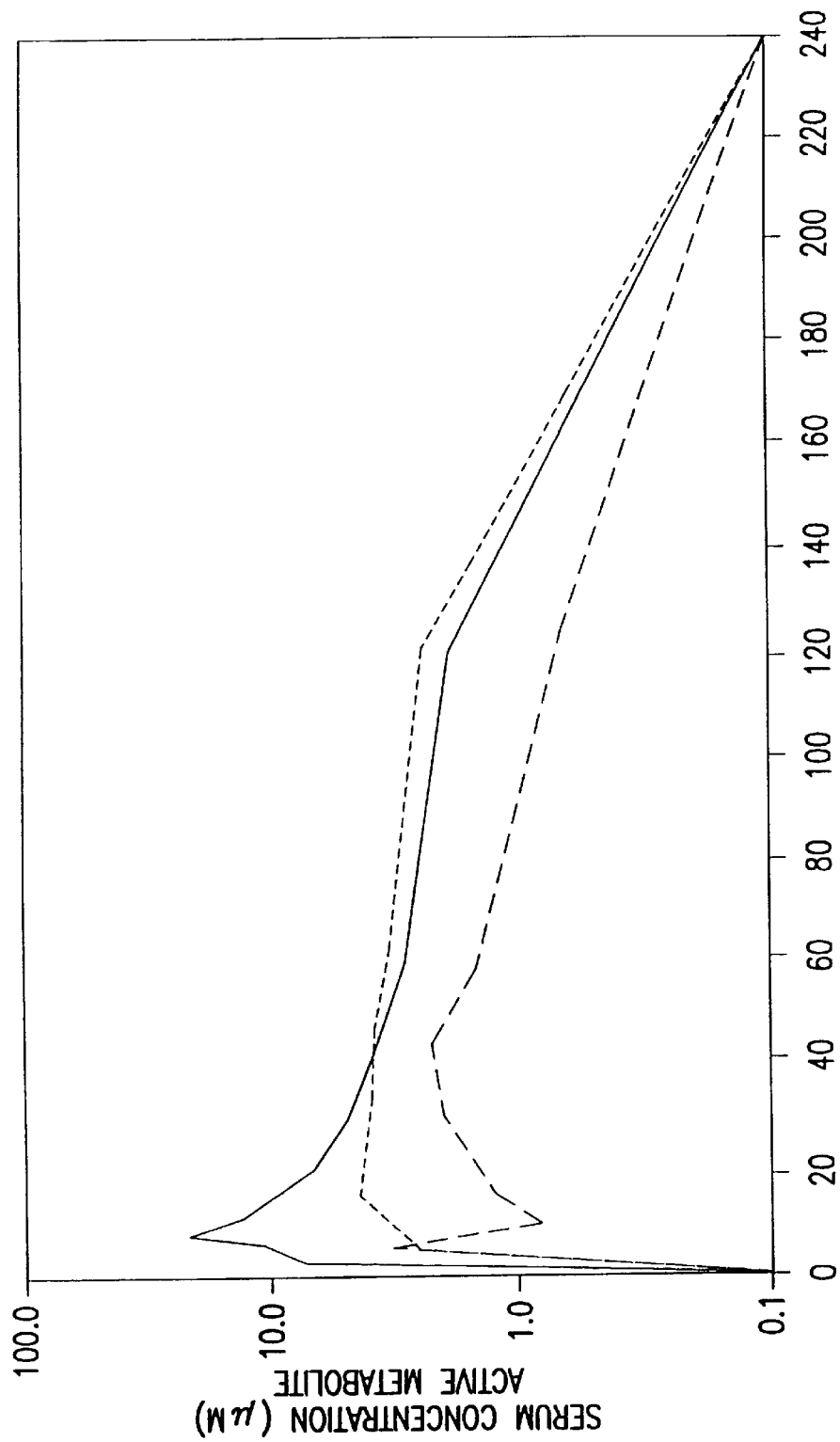
FIG. 3 is a graph of the average serum concentration-time curves for active metabolite (WR-1065) following a 500 mg subcutaneous injection, a 500 mg oral solution and a 200 mg/m$^2$ intravenous infusion (over 7.5 minutes) to 12 subjects, 0 to 240 minutes after drug administration (—— iv; ---sc; —— —— oral).

Analysis of the pharmacokinetic profiles of amifostine and its active metabolite WR-1065 following intravenous and subcutaneous administration of amifostine reveals several striking differences. Referring now to FIGS. 1–3, the pharmacokinetic profiles of amifostine (FIG. 2), an active metabolite of amifostine (WR-1065) (FIG. 3) and amifostine and WR-1065 combined (FIG. 1) obtained after intravenous administration of amifostine (200 mg/m² drug infused over 7.5 min.) are characterized by an initial plasma concentration "spike" or "burst" within the first 20 minutes following administration, a time-frame that coincides with the side effect observed clinically: infused drug and/or its active metabolite is rapidly taken up within the first minute of administration, reaching a maximum whole blood concentration approximately 8–10 minutes after administration, followed by a rapid (approx. 5–10 fold) decrease in concentration about 10–20 minutes after administration. Following this initial concentration "spike" or "burst," blood levels gradually decrease to zero.

Similar pharmacokinetic profiles were observed with amifostine in cancer patients following a single intravenous bolus dose (150 mg/M$^2$) (Shaw et al., 1986, "Human Pharmacokinetics of WR-2721" *Int. J. Radiat. Oncol. Biol. Phys.* 12:1501–4), a single 15-minute intravenous infusion (up to 910 mg/M$^2$) (Shaw et al., 1988, "Pharmacokinetics of WR-2721" *Pharmac. Ther.* 39:195–201; Shaw et al., 1994, "Pharmacokinetics of Amifostine in Cancer Patients: Evidence for Saturable Metabolism" *Proc. Amer. Cos. Clin. Oncol.* 13:144; U.S. Bioscience, 1994, "Pharmacokinetics of Single Dose Amifostine (WR-2721; Ethyol)" ETH PK 3) and repeated infusions (up to 910 mg/m$^2$ per dose) (U.S. Bioscience, 1994, "Pharmacokinetics of Double Dose Amifostine (WR-2721; Ethyol) with Corresponding Measurements of WR-1065 in Plasma and Bone Marrow Cells" ETH PK 4). In these studies, amifostine was rapidly cleared from the blood, exhibiting a distribution half-life of less than 1 minute and an elimination half-life of approximately 9 minutes.

The pharmacokinetic profiles of amifostine, active metabolite WR-1065 and amifostine and WR-1065 combined following subcutaneous administration of amifostine (500 mg dose) differ significantly from those obtained-with intravenous administration. First, referring now to FIGS. 1 and 3, maximum whole blood concentrations are not reached by way of an initial concentration spike or burst. Rather, blood concentrations rise at a significantly slower rate, reaching a maximum approximately in 5–60 minutes, preferably 10–40 minutes, after administration. Maximum levels plateau, being maintained for about 10 to 130 minutes, preferably about 15 to 120 minutes, before gradually decreasing to baseline levels.

Additionally, the maximum whole blood concentrations of both amifostine and WR-1065 were significantly lower following subcutaneous administration than intravenous administration. For example, for intravenous administration, peak levels for amifostine and WR-1065 were about 100 $\mu$M and about 23 $\mu$M, respectively. For subcutaneous administration, maximum blood levels for amifostine and WR-1065 were about 12 $\mu$M and 4 $\mu$M, respectively. These concentrations are biologically effective, both as a cytoprotective agent and in MDS (Dorr et al., 1995, *Eur. J. Cancer* 31a (supp. 5):579, List et al., 1995, *Blood* 86(10) Supp. 1:1327 (Abstract)).

Thus, the advantageous pharmacokinetic profiles of the invention are generally characterized by three main features:
(i) a first region wherein the plasma and/or whole blood concentration of administered compound (and/or an active metabolite thereof) slowly rises to a maximum level; (ii) a second region wherein the maximum plasma and/or whole blood concentration of administered compound (and/or an active metabolite thereof) plateaus; and (iii) a third region wherein the maximum plasma and/or whole blood concentration of administered compound (and/or an active metabolite thereof) slowly decreases to baseline levels.

In the first region of the pharmacokinetic profile, the plasma and/or blood concentration usually increases at a rate of about 0.1 $\mu$M/min. to 40 $\mu$M/min., preferably about 0.3 $\mu$M/min. to 20 $\mu$M/min., and most preferably about 0.5 $\mu$M/min. to 10 $\mu$M/min. This increase toward the maximum concentration usually occurs over a period of about 1 min. to 60 min., commonly over a period of about 5 min. to 25 min., typically over a period of about 10 min. to 20 min., and preferably over a period of about 15 min. The maximum plasma and/or blood concentration is usually reached in about 5 to 60 min. following administration, and is preferably reached about 12 min. to 18 min. following administration. The increase in plasma and/or blood concentrations in this first region is usually zero-order, i.e., the rate of increase is substantially constant during the period of rise.

The maximum plasma and/or blood concentration of administered compound (and/or an active metabolite thereof) reached at the end of the first region remains relatively constant, i.e. plateaus, in the second region of the pharmacokinetic profile. Preferably, the plasma and/or blood concentration does not fluctuate by more than about±75%. More preferably, the plasma and/or blood concentration does not fluctuate by more than +35%. The plateau is usually maintained for about 10 min. to 130 min., preferably about 15 min. to 120 min., and occurs about 15 min. to 80 min. after administration.

In the third region, the plasma and/or blood concentration of administered compound (and/or an active metabolite thereof) slowly decreases towards baseline levels. The rate of decrease in plasma and/or blood concentration is typically governed by the subject's metabolism, and is not believed to be a critical feature towards effecting a reduction or decrease in undesirable side-effects following administration. While the actual rate of decrease in the plasma and/or blood concentration of administered compound (or active metabolites thereof) will vary from subject to subject, the concentration usually decreases at a rate of about 0.001 $\mu$M/min. to 0.2 $\mu$M/min., over a period of about 30 min. to 220 min. The third region usually occurs about 60 min. to 180 min. following administration.

While not intending to be bound by any particular theory, it is believed that the reduction or decrease in adverse side-effects following administration is due to the characteristics of the above-described pharmacokinetic profile. The slow rate at which the plasma and/or blood concentration of administered compound (and/or an active metabolite thereof) increases to maximum, as well as maintenance of the maximum level for a period of time, are thought to be of particular importance. Thus, it is believed that the pharmacokinetic profiles of the invention decrease or reduce adverse side effects of the compounds by eliminating the initial "spike" or "burst" in compound and/or metabolite plasma and/or blood concentrations that are associated with conventional intravenous administration, and that are likely unnecessary for efficacy.

The actual maximum plasma and/or blood concentration of administered compound (and/or an active metabolite thereof) is not believed to be of critical importance in reducing or decreasing adverse side-effects. As long as the compounds are administered according to the pharmacokinetic profiles described herein, a reduction or decrease in undesirable side-effects should be observed regardless of the actual maximum plasma and/or blood concentration reached. Thus, as will be discussed in more detail in a later section, virtually any amount of compound that yields a plasma and/or whole/blood concentration of the administered compound, and/or an active metabolite thereof, that is therapeutically effective can be advantageously administered according to the pharmacokinetic profiles described herein. The maximum plasma and/or blood concentration will usually range from about 1 $\mu$M to 40 $\mu$M.

Uses of the Methods

The methods of the invention can be used to efficaciously administer the compounds described herein to patients to treat virtually any disorder that is now known or that is later discovered to be treatable with such compounds.

For example, as the compounds described herein are able to selectively protect normal tissues against the toxicities associated with ionizing radiation without adversely affecting the tumor response (Constine et al., 1986, "Protection by WR-2721 of Human Bone Marrow Function Following Irradiation" *Int. J. Radia. Oncol. Biol. Phys.* 12:1505–8; Liu et al., 1992, "Use of Radiation with or Without WR-2721 in Advanced Rectal Cancer" *Cancer* 69(11):2820–5; Wadler et al., 1993, "Pilot Trial of Cisplatin, Radiation and WR-2721 in Carcinoma of the Uterine Cervix: A New York Gynecologic Oncology Group Study" *J. Clin. Oncol.* 11(8):1511–6; Büntzel et al., 1996, "Ethyol (Amifostine) Provides Multilineage heatoprotection and Protection Against Nonhematologic Toxicities Reduced by Radiochemotherapy (RCT) of Head and Neck Cancer," *Blood* 88 (10) Supp. 1:448a [1781] [Abstract]), the methods described herein can be used to administer the compounds to cancer patients receiving radiation therapy.

The compounds described herein are also capable of selectively protecting normal tissues from the toxicities associated with cancer chemotherapeutic agents, including but not limited to, alkylating agents, platinum agents, anthracyclines and taxanes (Kemp et al., 1996, "Amifostine Pretreatment for Protection Against Cyclophosphamide-and Cisplatin-Induced Toxicities: Results of A Randomized Control Trial in Patients with Advanced Ovarian Cancer" *J. Clin. Oncol.* 14:2101–12; Wasserman et al., 1981 "Differential Protection Against Cytotoxic Chemotherapeutic Effects on Bone Marrow CFUs by WR-2721" *Cancer Clin. Trials* 4:3–6; Glover et al., 1986, "WR-2721 Protects Against the Hematologic Toxicity of Cyclophosphamide: A Controlled Phase II Trial" *J. Clin. Oncol.* 4:584–8; Schiller et al., 1996, "Amifostine, Cisplatin and Vinblastine in Metastic Nonsmall Cell Lung Cancer: A Report of High Response Rates and Prolonged Survival" *J. Clin. Oncol.* 14:1913–21; Dorr et al., 1995, "Selective Cardioprotection of Rat Heart Myocytes Exposed to DNA Zutercalating Agents Using Amifostine (AMI) and It's Dephospharylated Metabolite, WR-1065," *Eur. J. Cancer* 31a (Supp. 5):579; Betticher et al., 1995, "Carboplatin Combined with Amifostine, a Bone Marrow Protectant, in the Treatment of Non-Small Cell Lung Cancer: A Radomised Phase II Study" *Br. J. Cancer* 5:1551–5; DiPaola et al., 1996, "A Phase I Study of Amifostine and Paclitaxel in Patients with Advanced Malignancies" *Proc. Amer. Soc. Clin. Oncol.* 15:488 (1556) Abstract). Thus, the methods of the invention can also be used to advantageously administer the compounds described herein to cancer patients receiving chemotherapy.

The compounds described herein are also capable of stimulating bone marrow growth (WO 96/25045) and causing the bone marrow function to more rapidly recover following chemotherapy (List et al., "Amifostine Stimulated Formation of Multipotent Progenitor and Generated Macroscopic Colonies in Normal and Myelodysplastic Bone Marrow," *Proc. Am. Soc. Clin. Oncol.* 15:449 [1403] [Abstract]; List et al., 1996, "Amifostine Protects Primitive Hematopoietic Progenitors Against Chemotherapy Cytotoxicity," *Semin. Oncol.* 23 (4) Supp. 8:58–63). Thus, the methods of the invention further provide a useful means for administering these compounds to patients suffering from diseases requiring bone marrow growth, such as myelodysplastic syndrome (MDS), and to patients whose bone marrow has been exposed to chemotherapy. In addition, the methods of the invention also provide a useful means for administering the compounds to patients suffering from cancer and human immunodeficiency virus infection.

Administering aminoalkyl phosphorothioate and/or aminoalkyl thiol compounds to patients according to the methods of the invention provides myriad advantages over currently available intravenous modes of administration. A significant advantage is the reduction or decrease in undesirable side-effects suffered by patients receiving the therapy. Additionally, since the methods do not require i.v. injection, which is the mode of administration most disliked by patients, the methods described herein will generally provide better patient compliance. Further, the methods of the invention do not necessarily require administration by skilled practitioners, making the therapy more convenient for patients.

Formulation and Routes of Administration

The compounds described herein, or pharmaceutically acceptable addition salts or hydrates thereof, can be delivered to a patient so as to avoid or reduce undesirable side effects according to the invention using a wide variety of routes or modes of administration. The only requirement is that the compound, and/or an active metabolite thereof, be delivered according to the pharmacokinetic profiles described herein. Suitable routes of administration include, but are not limited to, inhalation, transdermal, oral, rectal, transmucosal, intestinal and parenteral administration, including intramuscular, subcutaneous and intravenous injections.

For any mode of administration, the actual amount of compound delivered, as well as the dosing schedule necessary to achieve the advantageous pharmacokinetic profiles described herein, will be depend, in part, on such factors as the bioavailability of the compound (and/or an active metabolite thereof), the disorder being treated, the desired therapeutic dose, and other factors that will be apparent to those of skill in the art. The actual amount delivered and dosing schedule can be readily determined by those of skill without undue experimentation by monitoring the blood plasma levels of administered compound and/or an active metabolite thereof, and adjusting the dosage or dosing schedule as necessary to achieve the desired pharmacokinetic profile.

For example, for intravenous administration the advantageous profiles of the invention can be obtained by utilizing a significantly slower rate of infusion than is conventionally used, or by using an ambulatory pump. Methods of obtaining the desired pharmacokinetic profiles via other modes of administration will be apparent to those of skill in the art, especially in light of the detailed disclosure provided herein.

The compounds described herein, or pharmaceutically acceptable salts and/or hydrates thereof, may be administered singly, in combination with other compounds of the invention, and/or in combination with other therapeutic agents, including cancer chemotherapeutic agents. The active compound(s) may be administered alone or in the form of a pharmaceutical composition, wherein the active compound(s) is in admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. It is preferred that the compounds be administered by continuous infusion subcutaneously over a period of 15 minutes to 24 hours. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Effective Dosages

Pharmaceutical compositions suitable for use with the present invention include compositions wherein the active ingredient is contained in a therapeutically effective amount, i.e., an amount effective to achieve its intended purpose. Of course, the actual amount of active ingredient will depend on, among other things, its intended purpose. For example, when administered to cancer patients as a cytoprotectant in conjunction with radiation or chemotherapy, such compositions will contain an amount of active ingredient effective to, inter alia, ameliorate the harmful effects of ionizing radiation or chemotherapeutic agents to normal tissues. When administered to patients suffering from diseases requiring bone marrow growth, such as MDS, or more rapid recovery of bone marrow function following chemotherapy, such compositions will contain an amount of active ingredient effective to stimulate bone marrow production or function, prevent the development of or alleviate the existing symptoms of, or prolong the survival of, the patient being treated. Determination of an effective amount is well within the capabilities of those skilled in the art, especially in light of the detailed disclosure herein.

For any compound described herein the therapeutically effective amount can be initially estimated from cell culture assays. For example, a dose can be formulated in animal models to achieve a circulating concentration range of compound, and/or an active metabolite thereof, that includes an effective concentration as determined in cell culture. Such information can be used to more accurately determine useful doses in humans. See, e.g., Washburn et al., 1976, "Prediction of the Effective Radioprotective Dose of WR-2721 in Humans Through an Interspecies Tissue Distribution Study" *Radiat. Res.* 66:100–5.

Therapeutically effective amounts for use in humans can also be estimated from animal models. For example, a dose for humans can be formulated to achieve a circulating concentration found to be effective in animals.

A therapeutically effective dose can also be estimated from human pharmacokinetic data. While not intending to be bound by any particular theory, it is believed that efficacy is related to a subject's total exposure to an applied dose of administered drug, and/or an active metabolite thereof, as determined by measuring the area under the blood concentration-time curve (AUC). Thus, a dose administered according to the methods of the invention that has an AUC of administered compound (and/or an active metabolite thereof) within about 50% of the AUC of a dose known to be effective for the indication being treated is expected to be effective. A dose that has an AUC of administered compound (and/or an active metabolite thereof) within about 70%, 80% or even 90% or more of the AUC of a known effective dose is preferred. Adjusting the dose to achieve maximal efficacy in humans based on the methods described above, particularly on the blood concentration and duration of administered compound and/or its active metabolites is well within the capabilities of the ordinarily skilled artisan.

For use as a cytoprotectant to selectively protect against the toxicities of ionizing radiation or chemotherapeutic agents, a circulating concentration of administered compound (and/or and active metabolite thereof) of about 2 $\mu$M to 100 $\mu$M is expected to be effective, with about 5 $\mu$M to 50 $\mu$M being preferred. Alternatively, or in addition, a tissue concentration of administered compound (and/or an active metabolite thereof) of about 4 $\mu$M to 700 $\mu$M is expected to be effective, with about 20 $\mu$M to 350 $\mu$M being preferred.

Usual patient doses for administration of amifostine and/or its active metabolite WR-1065 usually range from about 50 mg/day to 6000 mg/day, commonly from about 100 mg/day to 4000 mg/day, and typically from about 200 mg/day to 3500 mg/day. Stated in terms of patient body weight, usual dosages range from about 0.6 to 100 mg/kg/day, commonly from about 1.1 to 66 mg/kg/day, and typically from about 2.2 to 58 mg/kg/day. Stated in terms of patient body surface areas, usual dosages range from about 23 to 4000 mg/m$^2$/day, commonly from about 45 to 2666 mg/m$^2$/day, and typically from about 90 to 2333 mg/m$^2$/day.

For subcutaneous administration of amifostine and/or its active metabolite WR-1065 patient dosages usually range from about 50 mg/day to 1500 mg/day, commonly from about 100 mg/day to 1000 mg/day and typically from about 200 mg/day to 750 mg/day. Stated in terms of body weight, usual dosages range from 0.5 mg/kg/day to 25 mg/kg/day, commonly from about 1 mg/kg/day to 16 mg/kg/day and typically from about 3.3 mg/kg/day to 12.5 mg/kg/day. Stated in terms of patient body surface areas, usual doses range from about 22 mg/m$^2$/day to 1000 mg/m$^2$/day, commonly from about 45 mg/m$^2$/day to 666 mg/m$^2$/day and typically from about 133 mg/m$^2$/day to 500 mg/m$^2$/day.

For use as a radioprotectant against the toxicities of ionizing radiation or as a chemoprotectant against the toxicities of cancer therapy, the dose should be administered enough in advance of exposure to radiation or chemotherapy to provide effect. For i.v. administration, the dose is preferably administered within 30 min. prior to the administration of radiation or chemotherapy. For subcutaneous administration, the dose is preferably administered about 20 to 90 minutes prior to the administration of radiation therapy.

For use in treating diseases requiring bone marrow growth, such as MDS, or recovery of bone marrow function, a circulating concentration of administered compound (and/or an active metabolite thereof) of about 2 $\mu$M to 100 $\mu$M is expected to be effective. Alternatively, or in addition, a tissue concentration of administered compound (and/or an active metabolite thereof) of about 0.1 $\mu$M to 1000 $\mu$M is expected to be effective, with about 10 $\mu$M to 500 $\mu$M being preferred.

Usual patient doses for administration of amifostine and/or its active metabolite WR-1065 usually range from about 50 mg/day to 1000 mg/day, commonly from about 100 mg/day to 900 mg/day, and typically from about 200 mg/day to 800 mg/day. Stated in terms of patient body weight, usual dosages range from about 0.5 to 16 mg/kg/day, commonly from about 1.1 to 15 mg/kg/day, and typically from about 2.2 to 13.5 mg/kg/day. Stated in terms of patient body surface areas, usual dosages range from about 22 to 666 mg/m$^2$/day, commonly from about 45 to 600 mg/m$^2$/day, and typically from about 90 to 540 mg/m$^2$/day.

For subcutaneous administration of amifostine and/or its active metabolite WR-1065 patient dosages usually range from about 50 mg/day to 1200 mg/day, commonly from about 100 mg/day to 1100 mg/day and typically from about 200 mg/day to 1000 mg/day. Stated in terms of body weight, usual dosages range from 0.5 mg/kg/day to 20 mg/kg/day, commonly from about 1.1 mg/kg/day to 18 mg/kg/day and typically from about 2.2 mg/kg/day to 16.2 mg/kg/day. Stated in terms of patient body surface areas, usual doses range from about 22 mg/m$^2$/day to 800 mg/m$^2$/day, commonly from about 45 mg/m$^2$/day to 720 mg/m$^2$/day and typically from about 90 mg/m$^2$/day to 650 mg/m$^2$/day.

For other modes of administration, dosage amount and interval can be adjusted individually to provide effective plasma and/or tissue levels of the administered compound, and/or an active metabolite thereof, according to the pharmacokinetic profiles described herein, as previously described.

The actual amount of composition administered will, of course, be dependent on the subject being treated, the subject's weight, the severity of the affliction, the mode of administration and the judgement of the prescribing physician.

EXAMPLE

Subcutaneous Administration of Amifostine Reduces In Vivo Toxicities

The advantageous effects of subcutaneously administering amifostine to patients was demonstrated in a Phase I, randomized three-way crossover study. The study was conducted at one site in the United States.

Normal subjects were randomized to receive amifostine for three successive days as an intravenous infusion (200 mg/m$^2$), an oral formulation (500 mg) and a subcutaneous injection (500 mg) as described in TABLE 1. A total of 12 subjects were treated in the study.

TABLE 1

Treatment Scheme
(Three-Way Crossover Design)

|  | Day 1 | Day 2 | Day 3 |
| --- | --- | --- | --- |
| Sequence 1 | A | B | C |
| Sequence 2 | B | C | A |
| Sequence 3 | C | A | B |

Treatment A: Amifostine (200 mg/m$^2$) as a continuous intravenous infusion over 7.5 minutes.
Treatment B: Amifostine (500 mg) in liquid formulation as a single oral dose.
Treatment C: Amifostine (500 mg) as two simultaneous subcutaneous injections.

All subjects were sequestered at the study site from the evening before the administration of the first dose of study drug until the final whole blood sample was obtained. Whole blood samples were collected up to 4 hours after each dose of amifostine.

Eligible subjects included healthy, normal male volunteers between the ages of 18 and 35 years (inclusive). All subjects who entered the study had pretreatment values for complete blood counts (CBC), serum chemistries and urinalysis within ±10% of the normal range for the referring laboratory which were considered clinically insignificant by the inventors. Additionally, all subjects had a normal pretreatment electrocardiogram (EKG).

Subjects who were known to be human immunodeficiency virus (HIV) positive, active substance abusers or smokers (at least within the past 6 months) were excluded. Also excluded were subjects with pretreatment hypertension (systolic blood pressure >140 mm Hg), subjects with known cardiovascular disease, subjects with general or psychological conditions which would preclude them from completing the study or signing the informed consent, and subjects who were unwilling or unable to abstain from alcoholic beverages and all medications, including prescription and over-the-counter drugs and vitamins, for 7 days prior to study entry and for 3 days while participating in the study.

Preparation of Intravenous Amifostine

For intravenous infusion, each vial of amifostine (500 mg per vial, U.S. Bioscience, lot. no. C3017C) was reconstituted with 9.7 mL of 0.9% Sodium Chloride Injection, USP. The appropriate dose of amifostine (200 mg/m$^2$) was further diluted with 0.9% Sodium Chloride Injection, USP, to produce a volume of 50 mL for administration.

Preparation of Oral Amifostine

For oral administration, each vial of amifostine (500 mg per vial, U.S. Bioscience, lot. no. C3017C) was reconstituted with 5 mL of normal saline solution. The reconstituted solution was drawn up in a 10 mL syringe for administration.

Preparation of Subcutaneous Amifostine

For subcutaneous injection, each vial of amifostine (500 mg per vial, U.S. Bioscience, lot. no. C3017C) was reconstituted with 2.5 mL of normal saline solution. This solution was divided into two syringes (1.25 mL per syringe) for administration.

Administration of Intravenous Amifostine

Subjects received intravenous amifostine at a dose of 200 mg/M$^2$ as a 7.5 minute infusion (via an infusion pump) beginning at 8:00 $\mu$M. During the infusion, the subjects were kept in a supine position. Following amifostine administration, all subjects were allowed to have a standard breakfast. Moreover, all subjects were given a standard lunch at noon, a standard dinner at 6:00 $\mu$M and a standard snack at 10:00 $\mu$M.

Baseline systolic blood pressure and pulse were measured just prior to the amifostine infusion, every 2.5 minutes during the infusion and 5 minutes after the infusion. The amifostine infusion was interrupted if systolic blood pressure decreased as outlined in TABLE 2, or if the subject developed symptoms related to decreased blood pressure (dizziness, diaphoresis or chest pain).

If hypotension occurred, the subject was to receive a rapid infusion of normal saline and was to be kept supine or in the Treudelenburg position until the blood pressure returned to baseline. During this time, blood pressure was monitored every 3 minutes.

If blood pressure returned to the value stipulated in TABLE 2 within 5 minutes of stopping the amifostine infusion, and the subject was otherwise asymptomatic, the amifostine infusion could be restarted with continued frequent monitoring of blood pressure. If any further episode of hypotension occurred, the above guidelines were to be reapplied. If a subject's blood pressure did not return to the threshold value for restarting the amifostine infusion within 5 minutes of stopping the amifostine infusion, the infusion was to be stopped and any unused drug was discarded.

TABLE 2

Blood Pressure Guidelines for Interrupting and Starting Amifostine

| | Baseline Systolic Blood Pressure (mm Hg) | | | |
|---|---|---|---|---|
| | ≦110 | 111–130 | 131–150 | >170 |
| Stop infusion if systolic blood pressure decreases to: | ≦80 | ≦100 | ≦105 | ≦130 |
| Re-start infusion when systolic blood pressure returns to: | >80 | >100 | >120 | >130 |

Administration of Oral Amifostine

Subjects receiving oral amifostine were to fast (except for water) beginning at midnight the night before receiving the oral dose until noon of the following day when they received a standard lunch. On the day subjects received oral amifostine, ranitidine (50 mg) was administered by intravenous injection 1 hour prior to the start of amifostine administration.

Subjects received oral amifostine at a dose of 500 mg in a liquid formulation. This formulation was administered by gently squirting the solution in the back of the subject's throat. Subjects were kept in a supine position for 1 hour following administration of the oral solution of amifostine.

Following administration of amifostine, all subjects were allowed to drink 4 oz. of water and to eat hard candy to ameliorate any unpleasant taste from oral amifostine. All subjects were given a standard lunch at noon, a standard dinner at 6:00 $\mu$M and a standard snack at 10:00 $\mu$M.

Vital signs (blood pressure and pulse) were measured just prior to oral administration of amifostine and repeated every 5 minutes for 1 hour. If hypotension occurred, the subject was to receive a rapid infusion of 500 mL normal saline and was to be kept supine or in the Trendelenburg position until blood pressure returned to baseline. During this time, blood pressure was monitored every 3 minutes.

Administration of Subcutaneous Amifostine

Subcutaneous amifostine was administered at a dose of 500 mg (as a liquid formulation). The dose of amifostine was divided equally into two syringes and administered into two locations on the abdominal wall. Subjects were kept supine for 30 minutes following the two injections of amifostine. Following amifostine administration, all subjects were allowed to have a standard breakfast. All subjects were given a standard lunch at noon, a standard dinner at 6:00 $\mu$M and a standard snack at 10:00 $\mu$M.

Vital signs (blood pressure and pulse) were measured just prior to subcutaneous administration of amifostine and repeated every 5 minutes for 30 minutes. If hypotension occurred, the subject was to receive a rapid infusion of 500 mL normal saline and was to be kept supine or in the Trendelenburg position until blood pressure returned to baseline. During this time, blood pressure was monitored every 3 minutes.

Prior and Concomitant Medications

Ranitidine was administered to all subjects on the day amifostine was administered orally. Any subject who experienced Grade 2 or higher nausea and/or vomiting was allowed to receive prochlorperzaine (10 mg orally or by suppository) every 4 hours as needed.

Pretreatment Assessments

Pretreatment evaluations were performed within 7 days of initiating treatment and included the following:

- history and physical exam including height, weight and vital signs (blood pressure, pulse and temperature);
- CBC with differential and platelets;
- blood chemistries including blood urea nitrogen (BUN), serum creatinine, calcium, total bilirubin, albumin, SGOT, SGPT, alkaline phosphate, glucose and total protein;
- urinalysis; and
- EKG.

If any subject's laboratory parameters were abnormal, the laboratory tests were repeated. If upon retest the parameters were normal, the subject was included in the study. If the abnormal parameters persisted, the subject was excluded from the study.

Efficacy Assessments

The primary endpoint of this study was the relative bioavailability of 500 mg of amifostine administered subcutaneous or orally compared to 200 mg/m$^2$ of amifostine administered intravenously. As this was a crossover study in which each subject received amifostine by all three routes of administration, the bioavailabilities of subcutaneous and oral amifostine relative to intravenous amifostine were assessed within each subject.

Collection of Blood Samples

Blood samples (5 to 7 mL each) were collected either by venipuncture or indwelling venous catheter (IVC) heparin lock. If IVC was used, it was inserted in the arm opposite the infusion site. If central line was used, intravenous amifostine was administered by a distal intravenous site. For either line, the first 3 to 5 cc of blood were discarded (void volume) prior to blood collection.

For subjects receiving intravenous amifostine, blood samples were collected 5 minutes prior to amifostine administration (baseline) and 2.5, 5, 7.5, 10, 15, 20, 30 and 60 minutes, and 2 and 4 hours after amifostine administration.

For subjects receiving oral amifostine as a liquid formulation, blood samples were collected immediately prior to amifostine administration (baseline) and 5, 10, 15, 30, 45 and 60 minutes, and 2 and 4 hours after amifostine administration.

For subjects receiving subcutaneous amifostine, blood samples were collected immediately prior to amifostine administration (baseline) and 5, 10, 15, 30, 45 and 60 minutes, and 2 and 4 hours after amifostine administration.

Blood Sample Preparation

Blood samples were collected at specified times during a 4-hour period after each dose of amifostine. Each blood sample was prepared as described in TABLE 3. Blood samples were divided for purposes of analysis: one sample was used to determine the presence of amifostine, and the other sample was used to determine the presence of WR-1065 (active metabolite).

TABLE 3

Preparation of Plasma Samples for Determination of Concentrations of Amifostine and WR-1065

Whole blood was drawn into EDTA vacutainer tubeu on ice
↓                                               ↓
Removed 1.5 mL whole blood        Remainder of whole blood
and pipetted into                          after removing 1.5 mL
polypropylene tubes TABLE 3-continued Preparation of Plasma Samples for Determination of Concentrations of Amifostine and WR-1065 containing 1.5 mL PCA/EDTA
solution on ice
↓                                               ↓
Immediately mixed                  Centrifuged tubes at high
thoroughly by vortexing            speed for 5 minutes at 4° C.
↓                                               ↓
Centrifuged tubes at high          Plasma supernatant removed
speed for 10 minutes at 4° C.      into labelled polypropylene
                                               tubes on ice
↙              ↓                              ↓
Save       Clear supernatant removed    Store at −70° C. (these
Pellet     into labelled polypropylene   samples are for
           tubes on ice                  determination of
                                          amifostine)
↓                     ↓
Store at         Store at −70° C. (these
−70° C.          samples are for
                 determination of WR-1065,
                 the active metabolite)

EDTA is ethylenediaminetetraacetic acid
PCA is perchloric acid

As shown in TABLE 3, the preparation of amifostine (parent drug) and WR-1065 (active metabolite) for pharmacokinetic analysis differed from one another. This difference was based on the metabolic pathway of amifostine. Amifostine is a prodrug that is dephosphorylated at the tissue site by alkaline phosphatase to the active metabolite, WR-1065. WR-1065 can be further oxidized to form both symmetrical and mixed disulfides, or undergo further metabolism via copper-dependent amine oxidase to form acrolein and cysteamine. To prevent further oxidation of WR-1065, PCA/EDTA was added to the samples prior to centrifugation. Because PCA/EDTA ruptures the cellular content of the blood, the samples were centrifuged for a longer period of time to prevent contamination/metabolism of the active metabolite. Consequently, only the clear supernatant (serum) was used for analysis of WR-1065. In contrast, no PCA/EDTA was added to the blood samples designated for analysis of the parent drug; therefore, plasma samples were prepared for analysis of the parent drug.

Pharmacokinetic Analysis

Concentrations of amifostine (unchanged drug) and R-1065 (active metabolite) were measured using electrochemical-detection high-pressure liquid chromatography (HPLC) methods as described by Shaw, et al. (Shaw et al. 1984, "A Liquid Chromatographic Electrochemical Assay for S-2-(3-Aminopropylamino) ethylphosphorothioate (WR-2721) in Human Plasma," *J. Liq. Chromatog.* 7:2447–2465; Shaw et al., 1986, "Measurement of S-2-(3-Aminopropyl Amino) ethanethiol (WR-106S) in Blood and Tissue," *J. Liq. Chromatog.* 9:845–859). WINNONLIN, the WINDOWS version of PCNONLIN, was used for the determination of pharmacokinetic parameters for each subject following each route of administration. Non-compartmental modelling of the data was performed.

Safety Assessments

All subjects who had received at least one dose of protocol therapy were considered evaluable for safety. Safety was evaluated during and after administration of amifostine (prior to subjects leaving the study site) via analyses of adverse events, physical examination and laboratory tests. Toxicity notation was done after each dose of amifostine. Toxicity was based on National Cancer Institute (NCI) Common Toxicity Criteria.

The following safety evaluations were done after the last dose of amifostine (on Day 3) but prior to subjects leaving the study site:

physical exam including vital signs (blood pressure, pulse and temperature);

CBC with differential and platelets;

blood chemistries including BUN, serum creatinine, calcium, total bilirubin, albumin, SGOT, SGPT, alkaline phosphatase, glucose and total protein;

urinalysis; and toxicity notation.

Subjects who had abnormal laboratory values at discharge had those parameters repeated. If the parameters remained abnormal, the subject was referred to a physician of his choice for follow-up.

Sample Size Determination

Using a 3×3 latin square method with 12 subjects, the power to detect a 30% difference in area under the curve (AUC) for amifostine (parent drug) and WR-1065 was 80%. This difference was defined as a change in AUC values (67% more or 40% less) for one route of administration versus the other two routes of administration. The power calculation assumed a standard deviation of 50% of the mean AUC and a 70% correction with subjects.

Statistical Analysis

The primary endpoint of this study was the relative bioavailability of 500 mg of amifostine administered orally or subcutaneously compared to 200 mg/m$^2$ of amifostine administered intravenously. As this was a crossover study in which each subject received amifostine by all three routes of administration, the bioavailabilities of subcutaneous and oral amifostine relative to intravenous amifostine were assessed within each subject.

Bioavailability was assessed using area under the plasma/serum concentration-time curve (AUC) from 0 to 4 hours. AUCs were calculated using extrapolation according to a straightline from the last non-zero point.

The bioavailability of amifostine (parent drug plus active metabolite) following oral and subcutaneous administration was based on the ratio of AUCs of these routes of administration with the AUC of intravenous amifostine. The AUCs were then analyzed using an analysis of variance (ANOVA) model with route, period and subject as variables. Sequence was not included in the model as this variable was uniquely determined by route and period. The confidence interval on the ratio of the subcutaneous or oral route to the intravenous route was calculated using the mean square error from the entire ANOVA model.

Because this was a crossover study to be performed on three successive days, toxicities were assigned to the route of administration on the day the toxicity occurred. A full nonparametric crossover model (likelihood of ratio test) was used to assess toxicities which corrected for period and sequence effects. A PROC CATMOD of SAS@ was used for this analysis.

Results

Between Apr. 2, 1996 and Jul. 23, 1996, 12 healthy volunteers were enrolled onto this Phase I bioavailability study of amifostine given intravenously, orally and subcutaneously (Protocol WR-AO57). This study was conducted at one site in the United States. All 12 subjects completed the study as per the protocol.

A total of 12 healthy men enrolled onto Protocol WR-A057 (TABLE 4). The median age of these subjects was 25.5 years, ranging from 18 to 34 years. The median body surface area (BSA) was 1.84 m$^2$, ranging from 1.69 to 2.15 m$^2$. All subjects had normal pretreatment laboratory values within 10% of the normal range and no vital sign abnormalities prior to receiving study medication. Moreover, all subjects had normal pretreatment EKG.

TABLE 4

Baseline Demographic Characteristics of the 12 Subjects Who Received Amifostine Intravenously, Orally and Subcutaneously

| Parameter | Number (n = 12) | Percent |
|---|---|---|
| Age (years) | | |
| Median | 25.5 | |
| Range | 18–34 | |
| Race | | |
| Caucasian | 6 | (50.0%) |
| Black | 5 | (41.7%) |
| Other | 1 | (8.3%) |
| Body Surface Area (m$^2$) | | |
| Median | 1.84 | |
| Range | 1.69–2.15 | |
| Weight (kg) | | |
| Median | 70.2 | |
| Range | 59–91 | |
| Height (cm) | | |
| Median | 176.5 | |
| Range | 158–188 | |

Bioavailability

FIG. 1 shows the plasma/serum concentration-time curves for amifostine (parent drug plus active metabolite) following oral, subcutaneous and intravenous administration of amifostine in all 12 subjects. As seen in this figure, the shape of the plasma/serum concentration-time curves of the three routes of administration were markedly different. Following a 200 mg/m$^2$ intravenous infusion (over 7.5 minutes), there was rapid uptake of amifostine within <1 minute of drug administration. Thereafter, plasma/serum concentrations of amifostine decreased rapidly. The maximum concentration of amifostine was approximately 130 $\mu$M 8 to 10 minutes after intravenous administration which dropped below 10 $\mu$M 45 minutes after drug administration.

Following a 500 mg subcutaneous injection, there was a markedly slower rise in plasma/serum concentrations of amifostine as compared to intravenous administration. The maximum concentration of amifostine (approximately 15$\mu$M) was observed 15 minutes after subcutaneous administration and was maintained for approximately 30 minutes. Thereafter, concentrations of amifostine fell below 10 $\mu$M approximately 50 minutes after subcutaneous administration. Thirty minutes following administration of 200 mg/m$^2$ intravenous amifostine and 500 mg subcutaneous amifostine, the plasma/serum concentration-time curves of amifostine (parent drug plus active metabolite) were identical.

Following oral administration (500 mg as an liquid formulation), the maximum concentration of amifostine (approximately 5 $\mu$M) was observed 5 to 8 minutes after drug administration. Concentrations of amifostine dropped below 1.0 $\mu$M at 10 to 13 minutes after oral drug administration. A second peak of approximately 4 $\mu$M was observed 45 minutes after oral drug administration which dropped to approximately 1 $\mu$M at 60 minutes after drug administration.

FIG. 2 shows the average plasma concentration-time curves for amifostine (parent drug) following oral, subcutaneous and intravenous administration of amifostine to the 12 subjects. There was no detectable amount of parent drug in plasma samples of subjects following oral amifostine.

The shape of the plasma concentration-time curves of the intravenous and subcutaneous dose were similar to those seen in FIG. 1. Following the 200 mg/m² intravenous dose, there was rapid uptake of amifostine within <1 minute of drug administration. Thereafter, plasma concentrations of amifostine decreased rapidly. The maximum concentration of amifostine was approximately 100 µM 8 to 10 minutes after intravenous administration which dropped below 10 µM approximately 30 minutes after drug administration. Following a 500 mg subcutaneous injection, there was a slower rise in plasma concentrations of amifostine. The maximum concentration of amifostine (approximately 10 µM) was observed 15 minutes after subcutaneous and was maintained for approximately 30 minutes. Thereafter, concentrations of amifostine fell below 10 µM approximately 45 minutes after subcutaneous administration. Thirty minutes following administration of 200 mg/m² intravenous amifostine and 500 mg subcutaneous amifostine, the plasma concentration-time curves of the parent drug were similar but with higher concentrations of parent drug noted for subcutaneous amifostine versus intravenous amifostine.

FIG. 3 shows the average serum concentration-time curves for WR-1065 (active metabolite) following subcutaneous, oral and intravenous administration of amifostine in all 12 subjects. As seen in this figure, the shape of the serum concentration-time curves of the three routes of administration were similar to those observed in FIG. 1. In fact, the serum concentration-time curve for oral amifostine in FIG. 1 was the exact same curve as in FIG. 3; this is due to the fact that there was no detectable amount of parent drug in the plasma samples of subjects following oral amifostine. Following a 200 mg/m² intravenous infusion, there was rapid uptake of WR-1065 within <1 minute of drug administration. Thereafter, serum concentrations of WR-1065 also decreased rapidly but at a slower rate than that which was observed with the parent drug (see FIG. 2). The maximum concentration of WR-1065 was approximately 30 µM 10 minutes after intravenous administration which fell below 5 µM approximately 45 minutes after drug administration. Following a 500 mg subcutaneous injection, there was a slower rise in serum concentrations of WR-1065. The maximum concentration of WR-1065 (approximately 5 µM) was observed 15 minutes after subcutaneous administration and was maintained for approximately 30 minutes. Thereafter, concentrations of WR-1065 fell below 5 µM approximately 60 minutes after subcutaneous administration. Forty minutes following administration of 200 mg/m² intravenous amifostine and 500 mg subcutaneous amifostine, the serum concentration-time curves of the active metabolite were identical.

The primary endpoint of this study was the relative bioavailability of 500 mg amifostine administered orally or subcutaneously to 200 mg/m² amifostine administered intravenously. TABLE 5 lists the AUC values of amifostine (parent drug and active metabolite combined) for each subject following oral, subcutaneous and intravenous administration of amifostine. Based on the ratio of AUCs, the relative bioavailability of amifostine (parent drug and active metabolite) following a 500 mg subcutaneous dose was 0.67 (95% confidence interval of 0.37 to 0.98) of the 200 mg/M² intravenous dose. The relative bioavailability of amifostine following a 500 mg oral dose was 0.11 (95% confidence interval of 0.04 to 0.18) of the 200 mg/m² intravenous dose.

TABLE 5

Relative Bioavailability of 500 mg Amifostine Administered Orally or Subcutaneously to 200 mg/m² Amifostine Administered Intravenously in 12 Healthy, Male Subjects(Parent Drug and Active Metabolite Combined)

| | AUC (µMxmin) of Combined | | | Bioavailability | |
|---|---|---|---|---|---|
| Subject Number | 500 mg Subcutaneous (SC) | 500 mg Oral (PO) | 200 mg/m² Intravenous (IV) | Ratio PO/IV | Ratio SC/IV |
| 1001 | 1726 | 656 | 1573 | 0.42 | 1.10 |
| 1002 | 2411 | 243 | 2820 | 0.09 | 0.86 |
| 1003 | 3946 | 456 | 2432 | 0.19 | 1.62 |
| 1004 | 475 | 131 | 2198 | 0.66 | 0.22 |
| 1005 | 643 | 378 | 1383 | 0.27 | 0.46 |
| 1006 | 180 | 132 | 1876 | 0.07 | 0.10 |
| 1007 | 732 | 50 | 2102 | 0.02 | 0.35 |
| 1008 | 3080 | 42 | 1811 | 0.02 | 1.70 |
| 1009 | 550 | 86 | 1296 | 0.07 | 0.42 |
| 1010 | 348 | 0 | 1343 | 0.00 | 0.26 |
| 1011 | 985 | 121 | 1382 | 0.09 | 0.71 |
| 1012 | 550 | 2 | 1832 | 0.00 | 0.30 |
| Mean | 1302 | 191 | 1837 | 0.11 | 0.67 |
| 95% CI* | 611–1993 | 75–307 | 1565–2109 | 0.04–0.18 | 0.37–0.98 |

CI: confidence interval.
*Using the mean square error from the ANOVA model.

TABLE 6 lists the AUC values of the parent drug for each subject following oral, subcutaneous and intravenous administration of amifostine. Based on the ratio of AUCs, the relative bioavailability of the parent drug following a 500 mg subcutaneous dose was 0.72 (95% confidence interval of 0.26 to 1.18) of the 200 mg/M² intravenous dose. The relative bioavailability of the parent drug following a 500 mg oral dose was 0.00 as no parent drug was detected in blood samples of subjects following oral administration of amifostine (see FIG. 2).

TABLE 6

Relative Bioavailability of 500 mg Amifostine Administered Orally or Subcutaneously to 200 mg/m² Amifostine Administered Intravenously in 12 Healthy, Male Subjects(Parent Drug)

| | AUC (µMxmin) of Parent Drug | | | Bioavailability | |
|---|---|---|---|---|---|
| Subject Number | 500 mg Subcutaneous (SC) | 500 mg Oral (PO) | 200 mg/m² Intravenous (IV) | Ratio PO/IV | Ratio SC/IV |
| 1001 | 1208 | 0 | 840 | 0.00 | 1.44 |
| 1002 | 1135 | 0 | 1305 | 0.00 | 0.87 |
| 1003 | 2883 | 0 | 1238 | 0.00 | 2.33 |
| 1004 | 224 | 0 | 1759 | 0.00 | 0.13 |
| 1005 | 305 | 0 | 805 | 0.00 | 0.38 |
| 1006 | 0 | 0 | 1526 | 0.00 | 0.00 |
| 1007 | 515 | 0 | 1723 | 0.00 | 0.30 |
| 1008 | 2924 | 0 | 1378 | 0.00 | 2.12 |
| 1009 | 154 | 0 | 812 | 0.00 | 0.19 |
| 1010 | 264 | 0 | 928 | 0.00 | 0.28 |
| 1011 | 697 | 0 | 1156 | 0.00 | 0.60 |
| 1012 | 0 | 0 | 1351 | 0.00 | 0.00 |
| Mean | 859 | 0 | 1235 | 0.00 | 0.72 |
| 95% CI* | 274–1444 | — | 1044–1426 | — | 0.26–1.18 |

CI: confidence interval.
*Using the mean square error from the ANOVA model.

TABLE 7 lists the AUC values of the active metabolite (WR-1065) for each subject following oral, subcutaneous and intravenous administration of amifostine. Based on the ratio of AUCs, the relative bioavailability of the active metabolite following a 500 mg subcutaneous dose was 0.71 (95% confidence interval of 0.55 to 0.86) of the 200 mg/m² intravenous dose. The relative bioavailability of the active metabolite following a 500 mg oral dose was 0.32 (95% confidence interval of 0.16 to 0.48) of the 200 mg/m² intravenous dose.

TABLE 7

Relative Bioavailability of 500 mg Amifostine Administered Orally or Subcutaneously to 200 mg/m² Amifostine Administered Intravenously in 12 Healthy, Male Subjects(Active Metabolite)

| | AUC ($\mu$Mxmin) of Active | | | Bioavailability | |
|---|---|---|---|---|---|
| Subject Number | 500 mg Subcutaneous (SC) | 500 mg Oral (PO) | 200 mg/m² Intravenous (IV) | Ratio PO/IV | Ratio SC/IV |
| 1001 | 518 | 656 | 745 | 0.88 | 0.70 |
| 1002 | 1587 | 243 | 1583 | 0.15 | 1.00 |
| 1003 | 1047 | 456 | 1234 | 0.37 | 0.85 |
| 1004 | 251 | 131 | 424 | 0.31 | 0.59 |
| 1005 | 338 | 378 | 569 | 0.66 | 0.59 |
| 1006 | 180 | 132 | 265 | 0.50 | 0.68 |
| 1007 | 218 | 50 | 381 | 0.13 | 0.57 |
| 1008 | 142 | 42 | 437 | 0.10 | 0.32 |
| 1009 | 379 | 86 | 482 | 0.18 | 0.79 |
| 1010 | 84 | 0 | 338 | 0.00 | 0.25 |
| 1011 | 188 | 121 | 203 | 0.59 | 0.93 |
| 1012 | 550 | 2 | 457 | 0.00 | 1.20 |
| Mean | 457 | 191 | 593 | 0.32 | 0.71 |
| 95% CI* | 207–707 | 75–307 | 360–826 | 0.16–0.48 | 0.55–0.86 |

CI: confidence interval.
*Using the mean square error from the ANOVA model.

The aforementioned AUC data presented in TABLES 5, 6 and 7 were used to calculate the absolute bioavailability of amifostine following oral and subcutaneous administration. Using the 200 mg/M² intravenous dose as the dose representing 100% bioavailability, the AUC data for oral and subcutaneous amifostine were adjusted for dose and compared with the AUC data for intravenous amifostine. Based on the ratio of AUCs, in contrast to the relative bioavailabilities, the absolute bioavailability of amifostine (parent drug plus active metabolite) following subcutaneous administration was 0.50 (95% confidence interval of 0.27 to 0.73) of the intravenous dose. The absolute bioavailabilities of the parent drug and the active metabolite following subcutaneous administration were 0.53 (95% confidence interval of 0.18 to 0.88) and 0.53, respectively, (95% confidence interval of 0.41 to 0.64) of the intravenous dose. The absolute bioavailability of amifostine (parent drug plus active metabolite) following oral administration was 0.08 (95% confidence interval of 0.03 to 0.13) of the intravenous dose.

Efficacy

Plasma concentrations of amifostine (parent drug) and serum concentrations of WR-1065 (active metabolite) were measured in blood samples obtained from 12 heathy, male subjects prior to and up to 4 hours after receiving amifostine as a 500 mg subcutaneous injection, a 500 mg oral solution and a 200 mg/m² intravenous infusion (over 7.5 minutes). From these data, plasma/serum concentration-time curves were generated and used to determine the pharmacokinetic profile of amifostine (both parent drug and active metabolite) following each route of administration.

As shown in FIG. 1, the shapes of the plasma/serum concentration-time curves for amifostine (parent drug plus active metabolite) of the three routes of administration were different. Following all three routes of administration, there was rapid uptake of amifostine within 5 minutes of drug administration. The intravenous route exhibited the fastest rate of uptake, followed by the subcutaneous route and the oral route. Thereafter, plasma/serum concentrations of amifostine declined. The rate of decline was fastest for the intravenous route and slowest for the subcutaneous route. The maximum concentration of amifostine (parent drug plus active metabolite) following intravenous administration was approximately 130 $\mu$M (approximately 100 $\mu$M for parent drug and 30 $\mu$M for active metabolite). Maximum concentrations of amifostine (parent plus active metabolite) after subcutaneous and oral administration were approximately 15 $\mu$M and 5 $\mu$M, respectively. Maximum concentrations were reached at approximately 15 minutes and plateaued until approximately minutes of drug administration. As shown in FIG. 2, there was no detectable amount of parent drug in plasma samples of subjects following oral amifostine.

Adverse Events

TABLE 8 lists those subjects who reported an adverse event following intravenous, oral and subcutaneous administration of amifostine. No subject discontinued amifostine due to adverse events. All adverse events were mild in severity, transient and considered related to amifostine. Five subjects reported adverse events following intravenous amifostine versus one subject each following oral and subcutaneous amifostine. Nausea was the most common adverse event. Other adverse events included headache, hypotension, vomiting, lightheadedness and somnolence.

TABLE 8

List of Subjects Who Reported Adverse Events* Following Intravenous, Oral and Subcutaneous Administration of Amifostine (N = 12)

| Adverse Event | Intravenous | Oral | Subcutaneous |
|---|---|---|---|
| Headache | 1008 | | |
| Hypotension | 1003 | 1003 | |
| Nausea | 1001, 1003, 1005, 1007, 1008 | | 1002 |
| Vomiting | 1008 | | |
| Lightheadedness | 1003 | 1003 | |
| Somnolence | 1008 | | |

*All adverse events were mild in severity and related to amifostine.

Hypotension

Mild and transient episodes of hypotension were reported by one subject after intravenous and oral administration of amifostine (TABLE 10). On Day 2 of the study, Subject 1003 had a pre-infusion blood pressure reading of 115/58 mm Hg which decreased to 99/56 mm Hg, 5 minutes after completion of the infusion. Five minutes later, his blood pressure returned to baseline (114/56 mm Hg). Subject 1003 also experienced two episodes of hypotension following oral administration of amifostine on Day 3. With a baseline blood pressure reading of 121/70 mm Hg, transient decreases in blood pressure (99/49 and 98/51 mm Hg) were observed at 5 and 25 minutes after oral administration of amifostine, respectively. Thereafter, none of the other blood pressure readings met the criteria for hypotension.

There was no incidence of hypotension following subcutaneous administration of amifostine.

Emesis

Six subjects reported nausea and one subject vomited during the study. Nausea was reported in five subjects following intravenous amifostine and in one subject following subcutaneous amifostine (TABLE 10). Vomiting was reported in one subject following intravenous amifostine. All episodes of nausea/vomiting were mild in severity and transient in nature. Antiemetic therapy was prescribed in two subjects following intravenous amifostine. Subject 1007 received prochlorperazine (10 mg) for nausea, and Subject 1008 received prochlorperazine (10 mg) for nausea/vomiting.

Clinical Evaluations

Physical examinations including weight and vital signs (blood pressure, pulse and temperature) were performed after the last dose of amifostine but prior to subjects leaving the study site. No remarkable changes were noted in these parameters following the last dose of amifostine.

Clinical Laboratory Tests

Laboratory tests including hematology, serum chemistry and urinalysis were performed after the last dose of amifostine but prior to subjects leaving the study site. Laboratory results were compared to laboratory reference ranges as well as to NCI Common Toxicity Criteria. One subject (Subject 1010) had a serum creatinine value (0.60 mg/dL) >10% below the lower limit of the reference range (0.70 to 1.40 mg/dL); his baseline value was 0.90 mg/dL. This low value was considered by the inventors as clinically insignificant. In addition, none of the subjects experienced a Grade 2 or higher laboratory toxicity according to NCI Common Toxicity Criteria.

Safety Conclusions

Amifostine was well tolerated regardless of route of administration. All 12 subjects completed the required study medication as per the protocol. No subject discontinued amifostine due to adverse events. All adverse events were mild in severity, transient and considered related to amifostine. Five subjects reported adverse events following intravenous amifostine versus one subject each following oral and subcutaneous amifostine (TABLE 8). Nausea was the most common adverse event. Other adverse events included headache, hypotension, vomiting, lightheadedness and somnolence. Mild and transient episodes of hypotension were reported by one subject after intravenous and oral administration of amifostine. These episodes occurred after amifostine administration, and none lasted more than 5 minutes in duration. There was no incidence of hypotension following subcutaneous administration of amifostine. There were no remarkable findings for any of the clinical evaluations or clinical laboratory tests.

EXAMPLE

Subcutaneous Administration of Amifostine Protected Animals Against Radiation-Induced Mucositis One of the major limiting acute toxicities associated with radiotherapy is radiation-induced mucositis. The ability to reduce the duration and severity of acute mucosal reactions is of particular importance in the radiotherapy and/or chemotherapy of head and neck cancer. Therefore, the radioprotective effects of amifostine were examined in an experimental model of mucositis. In particular, the study compared the radioprotective effects of amifostine by subcutaneous (s.c.) and intraperitoneal (i.p.) administration. The mouse model developed by Parkins et al. was used to examine the mucosal reactions in the inferior lip of mice after irradiation, and this model has been established as a reproducible model in the art (Parkins et al., 1983, Radiother. Oncol. 1:159–165).

Experimental Design

C57BL/6 female mice of 8–10 weeks old were used and fed with semi liquid food. A total of 40 mice were randomly divided into eight treatment groups of five mice each. The treatment groups were:

Group 1: Saline solution (i.p.) and irradiation
Group 2: Saline solution (s.c.) and irradiation
Group 3: Amifostine (200 mg/Kg, i.p.) and irradiation
Group 4: Amifostine (400 mg/Kg, i.p.) and irradiation
Group 5: Amifostine (200 mg/Kg, s.c.) and irradiation
Group 6: Amifostine (400 mg/Kg, s.c.) and irradiation
Group 7: Saline solution (i.p.)
Group 8: Saline solution (s.c.)

Unanesthetized mice were maintained in supine position and irradiated exclusively on the tip of their mouth. They were immobilized using jigs comparable to those previously used by Ang et al. (1982, Int. J. Radiat. Oncol. Biol. Phys. 8:145–148). Irradiation was performed with a RT 250 Philips apparatus delivering 1.98 Gy per min. (200Kv, 20 mA, filter of 0.2 mm de Cu). During irradiation, a constant normobaric air renewal was maintained. The effects of amifostine were evaluated using a single dose of 16.5 Gy.

Administration of Amifostine

Amifostine was dissolved in physiological saline (0.9% Nacl to achieve a final concentration of 50 mg/ml) immediately before injections at 200 or 400 mg/Kg body weight. Both i.p. and s.c. injections were conducted 30 minutes before irradiation. A placebo solution of saline alone was used for the control group.

Mucositis Scoring System

The effects of irradiation on lip mucosa were evaluated using the scoring system described by Parkins et al. (1983, Radiother. Oncol. 1:159–165). Body weight of the treated mice were scored daily after treatment. Reduction in body weight was used as an objective indication of the severity of mucositis induced by irradiation, presumably resulting from the inability of the animals to eat. In this model, the acute reactions peaked around day 10 to 11 after irradiation.

Other symptoms of mucositis such as mucosal erythema and edema were also recorded. These symptoms developed more slowly than weight loss following irradiation. Mucosal erythema and edema were scored separately, and could be analyzed as separate scores or as a combined score yielding a maximum score of 7. Mouse lip mucosal erythema was scored according to Table 9.

TABLE 9

Scoring System for Mucosal Erythema

| Score | Mucosal Observation |
|---|---|
| 0.5 | doubtful if abnormally pink |
| 1 | slight but definitely reddening |
| 2 | severe reddening |
| 3 | focal desquamation |
| 4 | exudation or crusting covering about ½ lip area |
| 5 | exudation or crusting covering more than ½ lip area |

Mucosal edema (swelling) of the lips was scored according to Table 10.

TABLE 10

Scoring System for Mucosal Edema

| Score | Mucosal Observation |
|---|---|
| 0.5 | 50-50 doubtful if any swelling |
| 1 | slight but definitely swelling |
| 2 | sever swelling |

Results

Figure 4A:
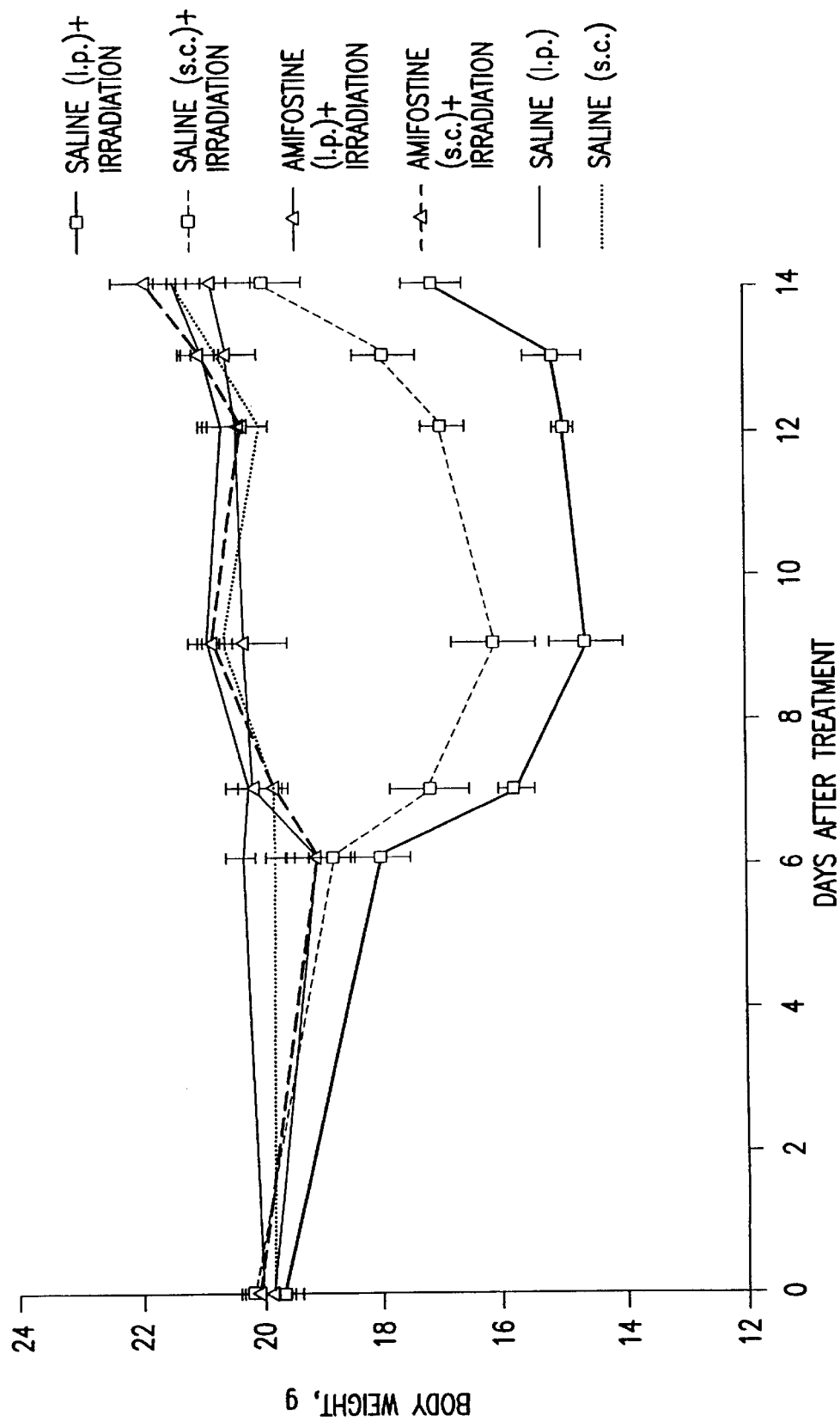
FIG. 4A and 4B are two graphs of the body weight of animals treated with amifostine or saline and a single dose of irradiation at 16.5 Gy. Amifostine and saline were administered by i.p. and s.c. routes. Control animals received saline without irradiation. Amifostine was dissolved at 500 mg in 9.7 ml of 0.9% Nacl to achieve a final concentration of 50 mg/ml. About 0.1–0.2 ml of amifostine was injected in each animal based on the body weight. Amifostine was administered at a dose of 400 mg/kg body weight (FIG. 4A) and at a dose of 200 mg/kg body weight (FIG. 4B).
Figure 4B:
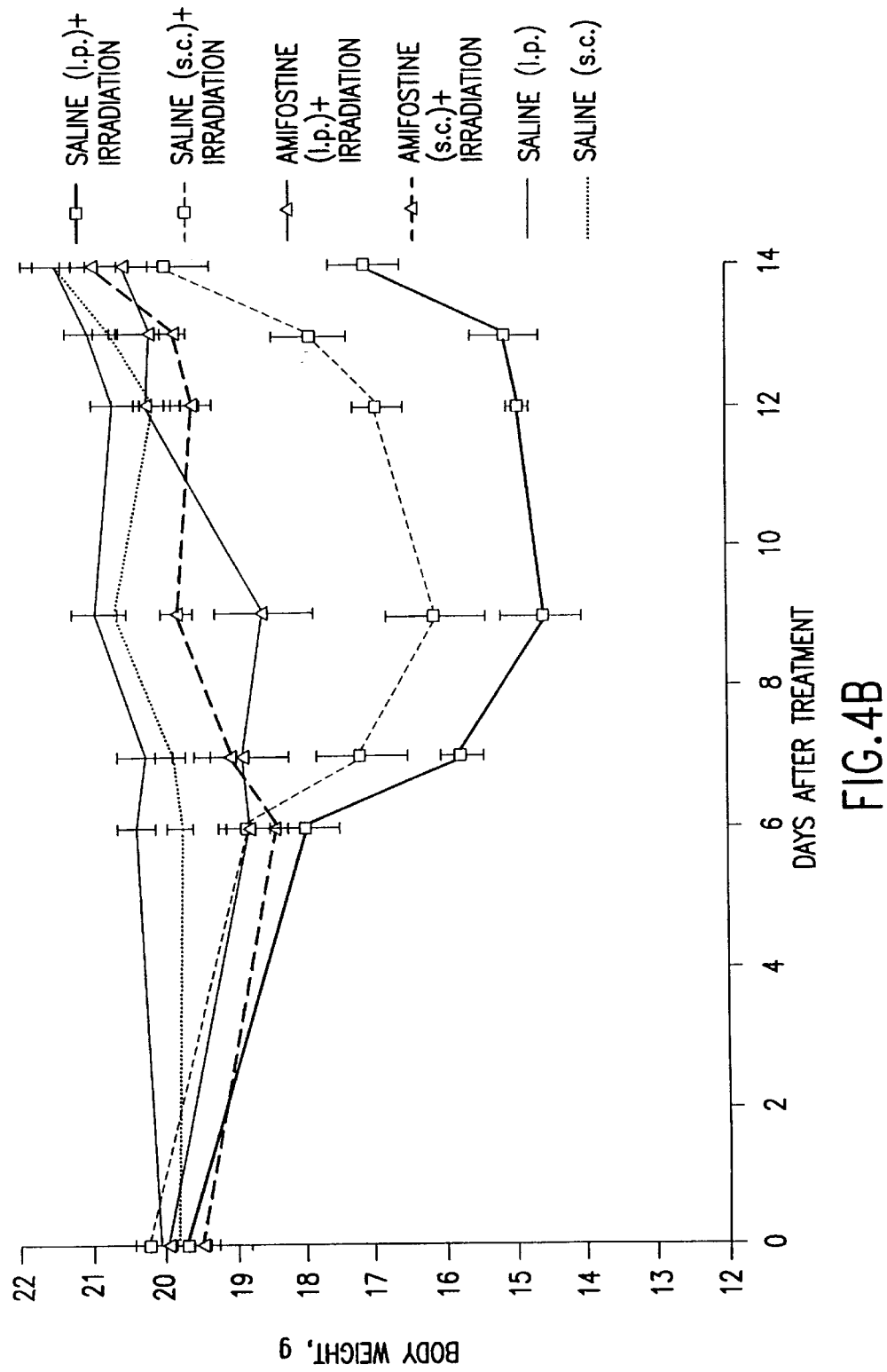

Body weight reduction of irradiated mice was measured as an objective indicator of mucositis (Table 11). A single dose of irradiation greatly reduced the body weight of the animals, particularly 7–13 days after treatment (FIG. 4A and 4B). Non-irradiated animals maintained steady body weight throughout the course of the study. Reduction in body weight was prevented in animals which received either i.p. or s.c. injection of amifostine. The radioprotective effects of amifostine were dose dependent.

Figure 5A:
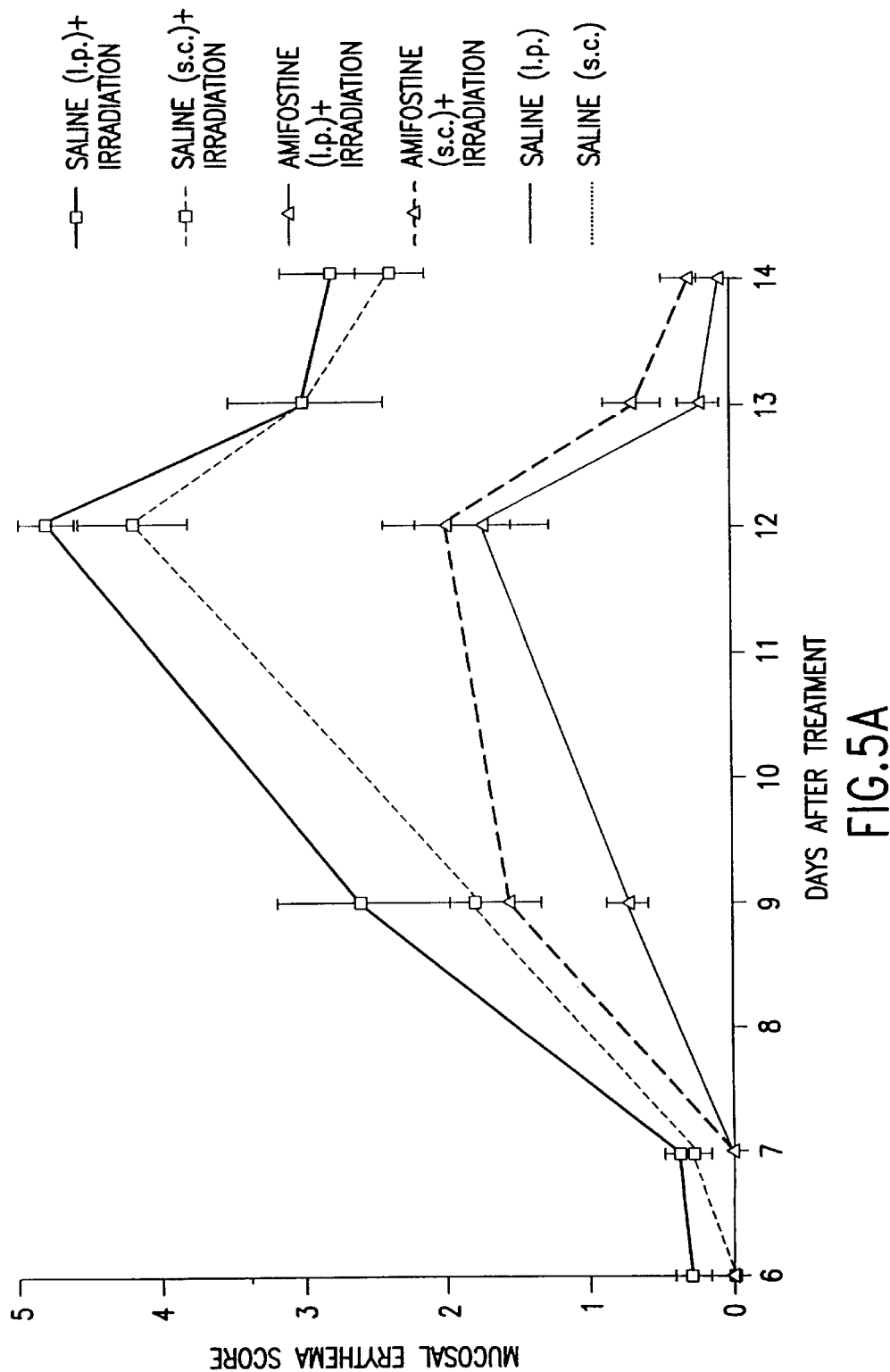
FIG. 5A and 5B are two graphs of the mucosal erythema scores of animals treated with amifostine or saline and a single dose of irradiation at 16.5 Gy. Amifostine and saline were administered by i.p. and s.c. routes. Control animals received saline without irradiation. Amifostine was dissolved at 500 mg in 9.7 ml of 0.9% Nacl to achieve a final concentration of 50 mg/ml. About 0.1–0.2 ml of amifostine was injected in each animal based on the body weight. Amifostine was administered at a dose of 400 mg/kg body weight (FIG. 5A) and at a dose of 200 mg/kg body weight (FIG. 5B).
Figure 5B:
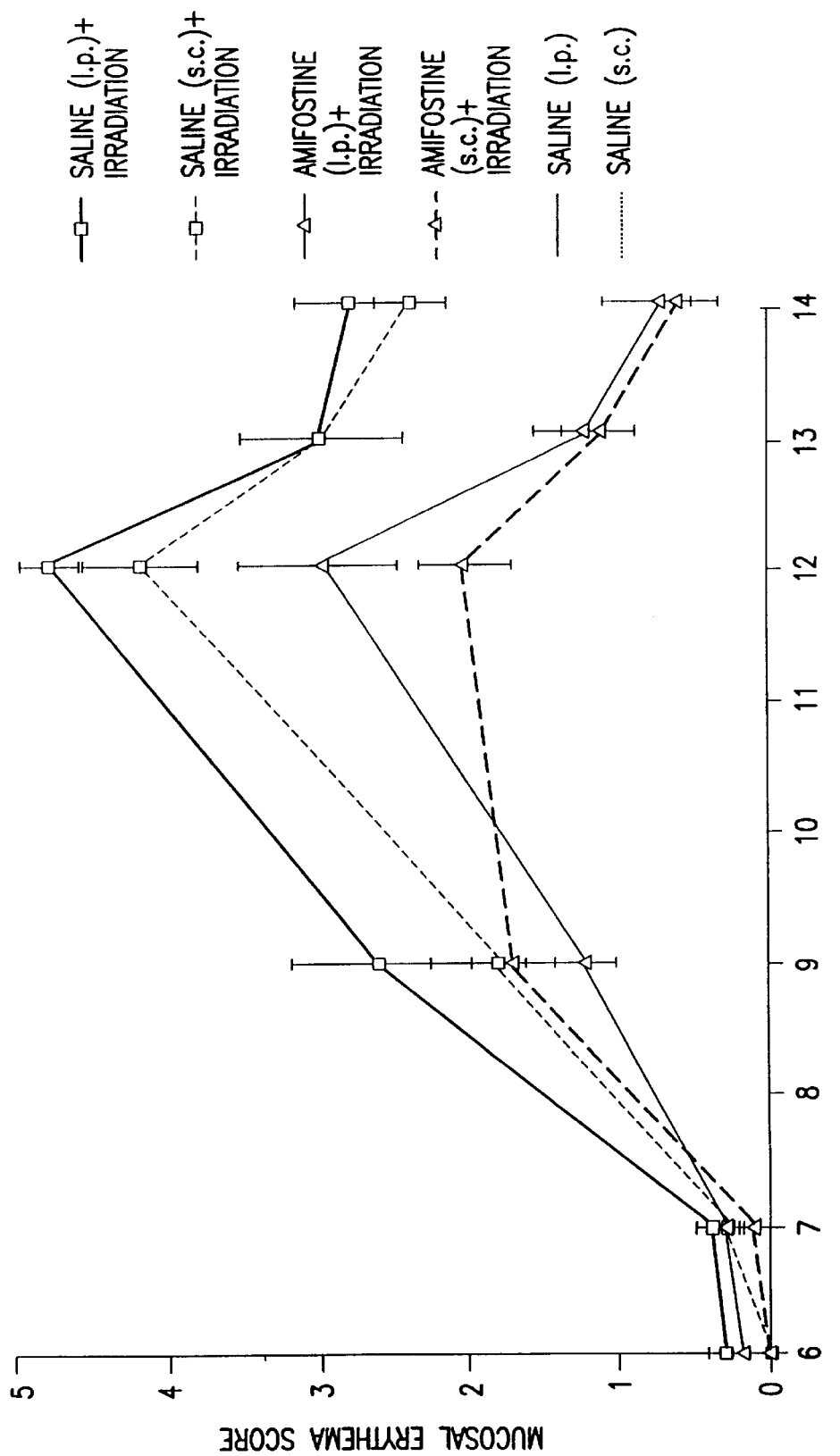
Figure 6A:
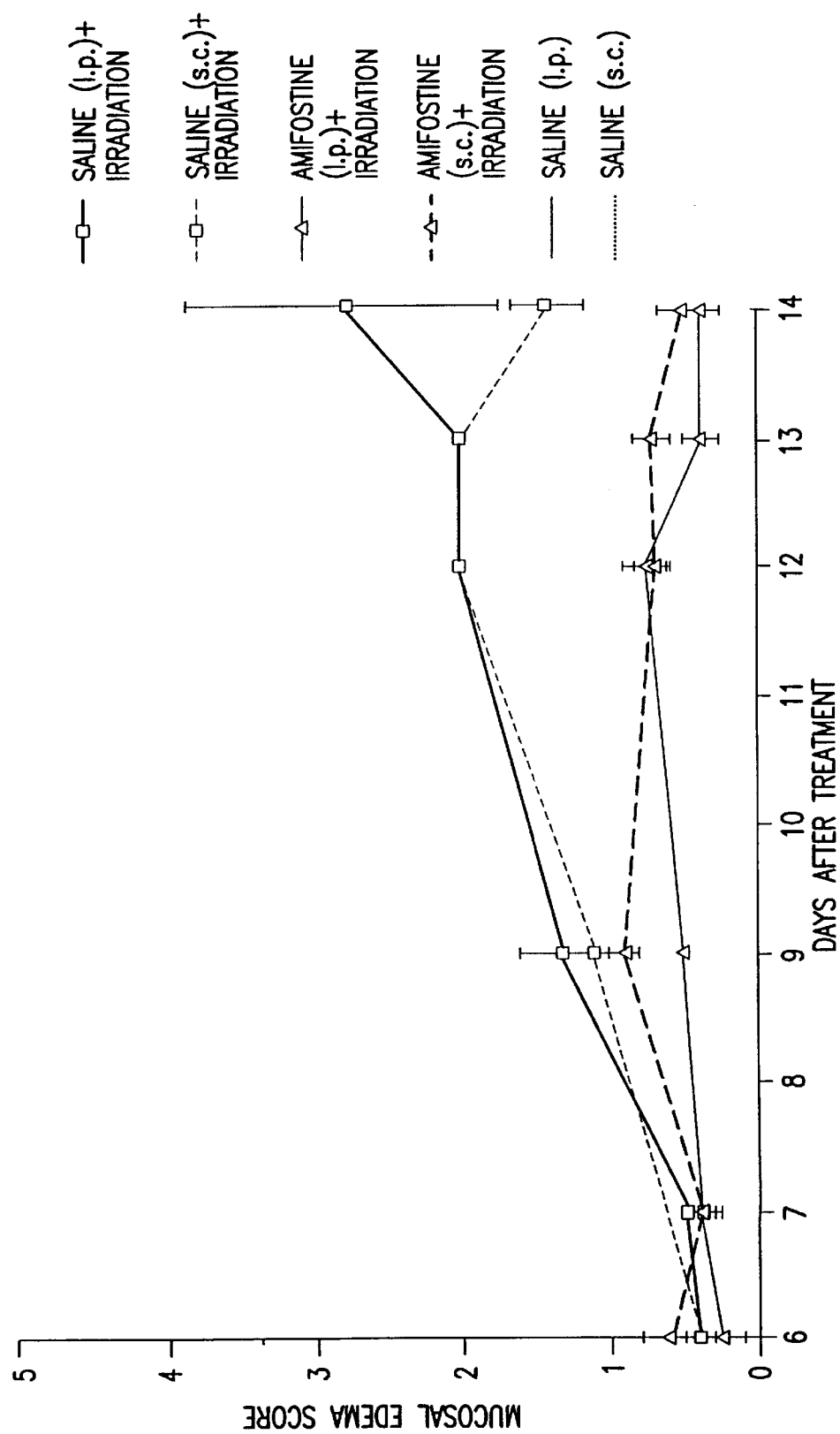
FIG. 6A and 6B are two graphs of the mucosal edema scores of animals treated with amifostine or saline and a single dose of irradiation at 16.5 Gy. Amifostine and saline were administered by i.p. and s.c. routes. Control animals received saline without irradiation. Amifostine was dissolved at 500 mg in 9.7 ml of 0.9% Nacl to achieve a final concentration of 50 mg/ml. About 0.1–0.2 ml of amifostine was injected in each animal based on the body weight. Amifostine was administered at a dose of 400 mg/kg body weight (FIG. 6A) and at a dose of 200 mg/kg body weight (FIG. 6B).
Figure 6B:
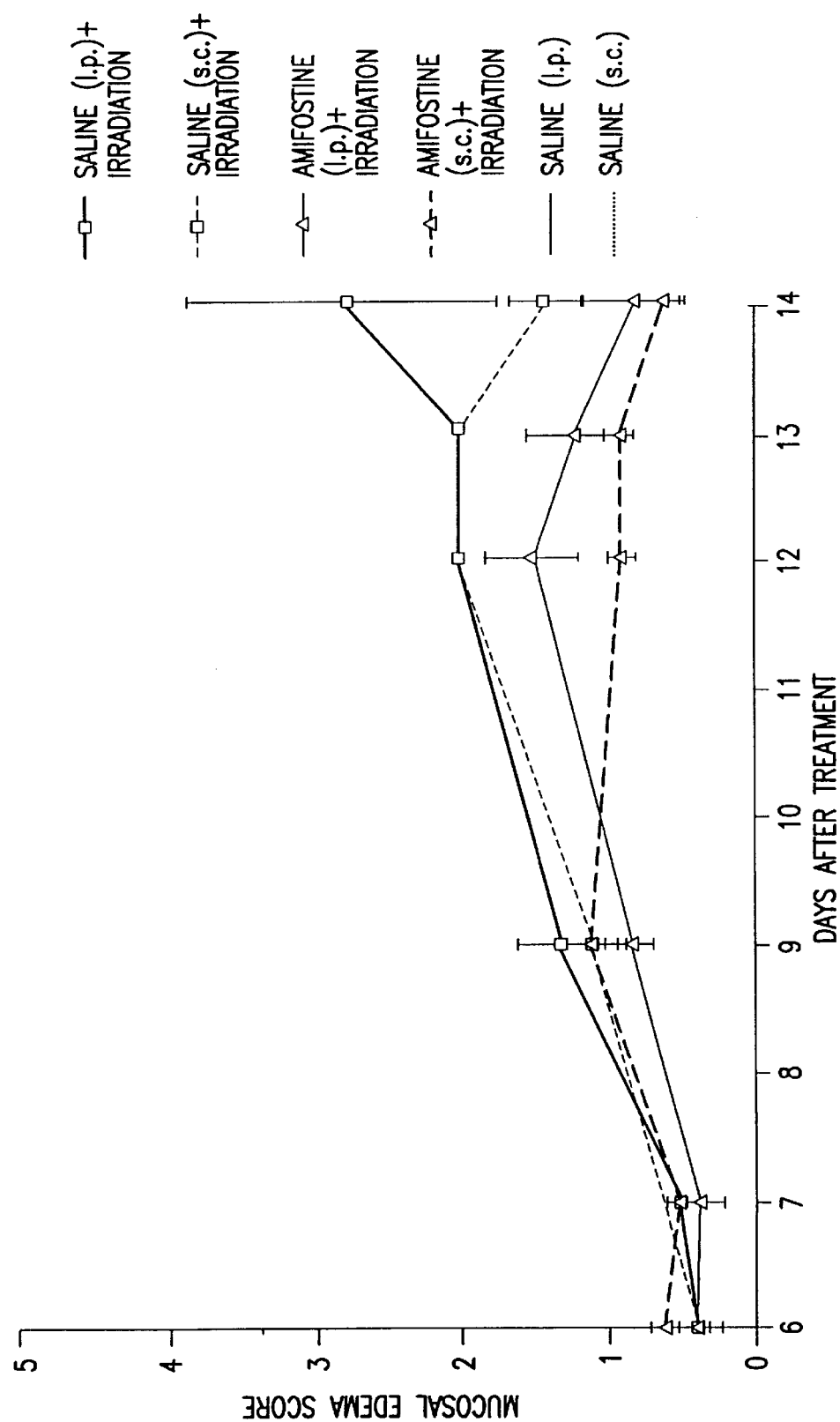

Non-irradiated mice had no erythema during the entire period of the experiment (Table 12). In contrast, erythema was observed in all irradiation groups (FIGS. 5A and 5B). Both i.p and s.c. administration of amifostine decreased the average erythema score as compared to saline plus irradiation. Similarly, mucosal edema scores were decreased by both injection methods of amifostine (FIGS. 6A and 6B, Table 13).

The data presented in FIGS. 4A, 4B, 5A, 5B, 6A, 6B and Tables 11–13 show that both s.c. and i.p. administration were effective in reducing the adverse effects of radiation, as measured by three mucositis indicators, i.e., body weight, erythema score and edema score. Furthermore, the subcutaneous administration of amifostine at 200 mg/kg produced the highest efficacy at the time points of maximal adverse effects (i.e., day 9 for body weight and day 12 for erythema and edema). An increase in the dose of amifostine from 200 mg/kg to 400 mg/kg produced minimal additional benefits. Thus, these results indicate that subcutaneously administered amifostine may have improved efficacy over other routes of administration, such as i.p.

TABLE 11

Body Weight

Saline (l.p.) + Irradiation

| Days | 0 | 6 | 7 | 9 | 12 | 13 | 14 |
|---|---|---|---|---|---|---|---|
| 1 | 20 | 19.8 | 16.3 | 16.5 | 15.1 | 15.5 | 18.4 |
| 2 | 20 | 17.4 | 14.6 | 13.3 | 14.3 | 13.87 | 15.4 |
| 3 | 20 | 17.8 | 16 | 13.9 | 14.8 | 15.6 | 16.9 |
| 4 | 19.5 | 16.8 | 15.6 | 13.7 | 15.2 | 16.4 | 17.9 |
| 5 | 19 | 18.2 | 16.1 | 15.4 | 15.1 | 14 | 16.8 |
| Mean | 19.7 | 18 | 15.72 | 14.56 | 14.9 | 15.074 | 17.08 |
| Standard | 0.2 | 0.505964 | 0.302324 | 0.601332 | 0.164317 | 0.490893 | 0.517107 |

Saline (s.c.) + Irradiation

| Mouse | 0 | 6 | 7 | 9 | 12 | 13 | 14 |
|---|---|---|---|---|---|---|---|
| 1 | 20 | 20.1 | 18.8 | 18 | 17.6 | 18.46 | 20.9 |
| 2 | 20 | 17.8 | 15.5 | 14.5 | 15.7 | 16 | 18.2 |
| 3 | 20 | 19 | 18.1 | 17.1 | 16.9 | 18.5 | 20.2 |
| 4 | 21 | 19 | 17.7 | 16.4 | 17.7 | 19 | 21.5 |
| 5 | 20 | 18.2 | 15.7 | 14.4 | 16.6 | 17.5 | 18.8 |
| Mean | 20.2 | 18.82 | 17.16 | 16.08 | 16.9 | 17.892 | 19.92 |
| Standard | 0.2 | 0.395474 | 0.661513 | 0.71232 | 0.364692 | 0.531662 | 0.622415 |

Amifostine (l.p.) at 200 mg/kg + Irradiation

| Mouse | 0 | 6 | 7 | 9 | 12 | 13 | 14 |
|---|---|---|---|---|---|---|---|
| 1 | 20 | 18.1 | 19.1 | 18 | 19.3 | 19.3 | 19.8 |
| 2 | 20 | 18.1 | 16.7 | 17 | 19.7 | 19.6 | 20.1 |
| 3 | 20 | 18.6 | 18.3 | 17.3 | 19.3 | 19.4 | 20 |
| 4 | 20 | 19 | 19.6 | 20.1 | 21.3 | 21.4 | 21.6 |
| 5 | 20 | 20 | 20.7 | 20.4 | 21.3 | 21 | 21 |
| Mean | 20 | 18.76 | 18.88 | 18.56 | 20.18 | 20.14 | 20.5 |
| Standard | 0 | 0.352987 | 0.669627 | 0.710352 | 0.463033 | 0.44 | 0.343511 |

Amifostine (l.p.) at 400 mg/kg + Irradiation

| Mouse | 0 | 6 | 7 | 9 | 12 | 13 | 14 |
|---|---|---|---|---|---|---|---|
| 1 | 20.5 | 19.7 | 20 | 20.4 | 21.2 | 20.8 | 21.6 |
| 2 | 19 | 18.1 | 19.4 | 18.2 | 18.7 | 19 | 18.8 |
| 3 | 21 | 19.2 | 20.7 | 21.8 | 21 | 21.3 | 21.8 |
| 4 | 19 | 19.4 | 20.4 | 20.8 | 20.8 | 21.2 | 21.1 |
| Mean | 19.875 | 19.1 | 20.125 | 20.3 | 20.425 | 20.575 | 20.825 |
| Standard | 0.515388 | 0.348807 | 0.280995 | 0.759386 | 0.580768 | 0.535996 | 0.690863 |

TABLE 11-continued

Body Weight

Amifostine (s.c.) at 200 mg/kg + Irradiation

| Mouse | 0 | 6 | 7 | 9 | 12 | 13 | 14 |
|---|---|---|---|---|---|---|---|
| 1 | 20 | 17.7 | 18.3 | 19.4 | 18.6 | 19.2 | 19.8 |
| 2 | 20 | 18.8 | 19.9 | 20.6 | 19.5 | 19.8 | 20.9 |
| 3 | 19.5 | 18.2 | 19.3 | 19.6 | 19.5 | 19.7 | 20.2 |
| 4 | 19 | 18.7 | 19 | 19.5 | 20.3 | 20.3 | 22.2 |
| 5 | 19 | 18.9 | 18.8 | 19.8 | 19.9 | 20 | 21.5 |
| Mean | 19.5 | 18.46 | 19.06 | 19.78 | 19.56 | 19.8 | 20.92 |
| Standard | 0.223607 | 0.224944 | 0.265707 | 0.215407 | 0.282135 | 0.181659 | 0.432897 |

Amifostine (s.c.) at 400 mg/kg + Irradiation

| Mouse | 0 | 6 | 7 | 9 | 12 | 13 | 14 |
|---|---|---|---|---|---|---|---|
| 1 | 20 | 19 | 19.4 | 20.6 | 19.9 | 20.5 | 21.4 |
| 2 | 20 | 19.7 | 19.8 | 20.8 | 18.8 | 20.3 | 21 |
| 3 | 19.5 | 20 | 20.6 | 21.4 | 20.7 | 21.1 | 21.4 |
| 4 | 21 | 16.9 | 19.2 | 20.7 | 21.7 | 22 | 24 |
| 5 | 20 | 19.6 | 20 | 20.7 | 20.8 | 21.3 | 21.7 |
| Mean | 20.1 | 19.04 | 19.8 | 20.84 | 20.38 | 21.04 | 21.9 |
| Standard | 0.244949 | 0.559106 | 0.244949 | 0.143527 | 0.487237 | 0.302655 | 0.536656 |

Saline (l.p.)

| Mouse | 0 | 6 | 7 | 9 | 12 | 13 | 14 |
|---|---|---|---|---|---|---|---|
| 1 | 20 | 20.7 | 19.8 | 20.4 | 19.9 | 20.7 | 20.9 |
| 2 | 19.3 | 19.6 | 19.1 | 20.5 | 20.1 | 19.9 | 20.5 |
| 3 | 20.6 | 21.1 | 21.1 | 21.5 | 21.5 | 21.5 | 23.1 |
| 4 | 19.3 | 20.2 | 20.1 | 20.3 | 20.6 | 21.2 | 21.1 |
| 5 | 21 | 20.1 | 21 | 21.8 | 21.1 | 21.6 | 21.6 |
| Mean | 20.04 | 20.34 | 20.22 | 20.9 | 20.64 | 20.98 | 21.44 |
| Standard | 0.341467 | 0.25807 | 0.376032 | 0.311448 | 0.299333 | 0.31209 | 0.451221 |

Saline (s.c.)

| Mouse | 0 | 6 | 7 | 9 | 12 | 13 | 14 |
|---|---|---|---|---|---|---|---|
| 1 | 20 | 19.8 | 19.7 | 20.7 | 20 | 20.7 | 21.5 |
| 2 | 19.3 | 19.2 | 19.4 | 20.i | 19.8 | 20.3 | 20.9 |
| 3 | 20.5 | 20 | 20.4 | 21 | 20.1 | 21 | 21.6 |
| 4 | 20.2 | 20.1 | 20.3 | 21 | 20.2 | 20.8 | 21.3 |
| 5 | 20 | 20.2 | 20.2 | 21.1 | 20.8 | 21.4 | 22.6 |
| 6 | 19 | 19.2 | 19.2 | 20.1 | 19.6 | 20.2 | 20.9 |
| Mean | 19.83333 | 19.75 | 19.86667 | 20.66667 | 20.08333 | 20.73333 | 21.46667 |
| Standard | 0.2319 | 0.182117 | 0.20602 | 0.18738 | 0.16816 | 0.181965 | 0.256472 |

TABLE 12

Erythema
Days after treatment

| Mouse | 6 | 7 | 9 | 12 | 13 | 14 |
|---|---|---|---|---|---|---|
| | | Saline (l.p.) + Irradiation | | | | |
| 1 | 0.5 | 0 | 2 | 5 | 2 | 2 |
| 2 | 0 | 0.5 | 4 | 4 | 3 | 3 |
| 3 | 0.5 | 0.5 | 4 | 5 | 5 | 4 |
| 4 | 0.5 | 0.5 | 1 | 5 | 2 | 3 |
| 5 | 0 | 0.5 | 2 | 5 | 3 | 2 |
| Mean | 0.3 | 0.4 | 2.6 | 4.8 | 3 | 2.8 |
| Standard | 0.122474 | 0.1 | 0.6 | 0.2 | 0.547723 | 0.374166 |
| | | Saline (s.c.) + Irradiation | | | | |
| 1 | 0 | 0.5 | 2 | 4 | 3 | 2 |
| 2 | 0 | 0.5 | 2 | 5 | 3 | 3 |
| 3 | 0 | 0 | 2 | 5 | 5 | 3 |
| 4 | 0 | 0 | 2 | 4 | 2 | 2 |

TABLE 12-continued

Erythema
Days after treatment

| Mouse | 6 | 7 | 9 | 12 | 13 | 14 |
|---|---|---|---|---|---|---|
| 5 | 0 | 0.5 | 1 | 3 | 2 | 2 |
| Mean | 0 | 0.3 | 1.8 | 4.2 | 3 | 2.4 |
| Standard | 0 | 0.122474 | 0.2 | 0.374166 | 0.547723 | 0.244949 |
| Amifostine (l.p.) at 200 mg/kg + Irradiation | | | | | | |
| 1 | 0.5 | 0.5 | 1 | 4 | 0.5 | 0.5 |
| 2 | 0 | 0 | 2 | 4 | 2 | 2 |
| 3 | 0 | 0 | 1 | 3 | 2 | 1 |
| 4 | 0.5 | 0.5 | 1 | 3 | 1 | 0 |
| 5 | 0 | 0 | 1 | 1 | 0.5 | 0 |
| Mean | 0.2 | 0.3 | 1.2 | 3 | 1.2 | 0.7 |
| Standard | 0.122474 | 0.122474 | 0.2 | 0.547723 | 0.339116 | 0.374166 |
| Amifostine (l.p.) at 400 mg/kg + Irradiation | | | | | | |
| 1 | 0 | 0 | 0.5 | 3 | 0 | 0 |
| 2 | 0 | 0 | 1 | 1 | 0.5 | 0.5 |
| 3 | 0 | 0 | 0.5 | 1 | 0.5 | 0 |
| 4 | 0 | 0 | 1 | 2 | 0 | 0 |
| Mean | 0 | 0 | 0.75 | 1.75 | 0.25 | 0.125 |
| Standard | 0 | 0 | 0.144338 | 0.478714 | 0.144338 | 0.125 |
| Amifostine (s.c.) at 200 mg/kg + Irradiation | | | | | | |
| 1 | 0 | 0 | 0.5 | 2 | 1 | 0.5 |
| 2 | 0 | 0 | 1 | 2 | 0.5 | 0.5 |
| 3 | 0 | 0.5 | 1 | 1 | 2 | 0.5 |
| 4 | 0 | 0 | 3 | 2 | 1 | 0.5 |
| 5 | 0 | 0 | 3 | 3 | 1 | 1 |
| Mean | 0 | 0.1 | 1.7 | 2 | 1.1 | 0.6 |
| Standard | 0 | 0.1 | 0.538516 | 0.316228 | 0.244949 | 0.1 |
| Amifostine (s.c.) at 400 mg/kg + Irradiation | | | | | | |
| 1 | 0 | 0 | 2 | 3 | 1 | 1 |
| 2 | 0 | 0 | 1 | 1 | 0 | 0 |
| 3 | 0 | 0 | 2 | 1 | 0.5 | 0 |
| 4 | 0 | 0 | 2 | 3 | 1 | 0 |
| 5 | 0 | 0 | 1 | 2 | 1 | 0.5 |
| Mean | 0 | 0 | 1.6 | 2 | 0.7 | 0.3 |
| Standard | 0 | 0 | 0.244949 | 0.447214 | 0.2 | 0.2 |
| Saline (l.p.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| Mean | 0 | 0 | 0 | 0 | 0 | 0 |
| Standard | 0 | 0 | 0 | 0 | 0 | 0 |
| Saline (s.c.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| Mean | 0 | 0 | 0 | 0 | 0 | 0 |
| Standard | 0 | 0 | 0 | 0 | 0 | 0 |

TABLE 13

| Mouse | Oedema Days after treatment | | | | | |
|---|---|---|---|---|---|---|
| | 6 | 7 | 9 | 12 | 13 | 14 |
| Saline (l.p.) + Irradiation | | | | | | |
| 1 | 0.5 | 0.5 | 1 | 2 | 2 | 1 |
| 2 | 0 | 0.5 | 0.5 | 2 | 2 | 2 |
| 3 | 0.5 | 0.5 | 2 | 2 | 2 | 2 |
| 4 | 0.5 | 0.5 | 1 | 2 | 2 | 2 |
| 5 | 0.5 | 0.5 | 2 | 2 | 2 | 7 |
| Mean | 0.4 | 0.5 | 1.3 | 2 | 2 | 2.8 |
| Standard | 0.1 | 0 | 0.3 | 0 | 0 | 1.067708 |
| Saline (s.c.) + Irradiation | | | | | | |
| 1 | 0 | 1 | 2 | 2 | 1 | |
| 2 | 0.5 | 1 | 2 | 2 | 2 | |
| 3 | 0.5 | 0.5 | 2 | 2 | 1 | |
| 4 | 0.5 | 1 | 2 | 2 | 1 | |
| 5 | 0.5 | 2 | 2 | 2 | 2 | |
| Mean | 0.4 | 1.1 | 2 | 2 | 1.4 | |
| Standard | 0.1 | 0.244949 | 0 | 0 | 0.244949 | |
| Amifostine (l.p.) at 200 mg/kg + Irradiation | | | | | | |
| 1 | 1 | 1 | 1 | 2 | 0.5 | 0.5 |
| 2 | 0 | 0 | 1 | 2 | 2 | 2 |
| 3 | 0.5 | 0.5 | 1 | 2 | 2 | 1 |
| 4 | 0.5 | 0.5 | 0.5 | 1 | 1 | 0.5 |
| 5 | 0 | 0 | 0.5 | 0.5 | 0.5 | 0 |
| Mean | 0.4 | 0.4 | 0.8 | 1.5 | 1.2 | 0.8 |
| Standard | 0.187083 | 0.187083 | 0.122474 | 0.316228 | 0.339116 | 0.339116 |
| Amifostine (l.p.) at 400 mg/kg + Irradiation | | | | | | |
| 1 | 0.5 | 0.5 | 0.5 | 1 | 0.5 | 0.5 |
| 2 | 0 | 0 | 0.5 | 0.5 | 0.5 | 0.5 |
| 3 | 0.5 | 0.5 | 0.5 | 0.5 | 0 | 0 |
| 4 | 0 | 0.5 | 0.5 | 1 | 0.5 | 0.5 |
| Mean | 0.25 | 0.375 | 0.5 | 0.75 | 0.375 | 0.375 |
| Standard | 0.144338 | 0.125 | 0 | 0.144338 | 0.125 | 0.125 |
| Amifostine (s.c.) at 200 mg/kg + Irradiation | | | | | | |
| 1 | 0.5 | 0.5 | 0.5 | 1 | 0.5 | 0.5 |
| 2 | 1 | 0.5 | 1 | 1 | 1 | 1 |
| 3 | 0.5 | 0.5 | 1 | 0.5 | 1 | 0.5 |
| 4 | 0.5 | 0.5 | 1 | 1 | 1 | 0 |
| 5 | 0.5 | 0.5 | 2 | 1 | 1 | 1 |
| Mean | 0.6 | 0.5 | 1.1 | 0.9 | 0.9 | 0.6 |
| Standard | 0.1 | 0 | 0.244949 | 0.1 | 0.1 | 0.187083 |
| Amifostine (s.c.) at 400 mg/kg + Irradiation | | | | | | |
| 1 | 1 | 0.5 | 1 | 0.5 | 0.5 | 1 |
| 2 | 0.5 | 0.5 | 0.5 | 0.5 | 0.5 | 0 |
| 3 | 0.5 | 0 | 1 | 0.5 | 0.5 | 0.5 |
| 4 | 1 | 0.5 | 1 | 1 | 1 | 0.5 |
| 5 | 0 | 0.5 | 1 | 1 | 1 | 0.5 |
| Mean | 0.6 | 0.4 | 0.9 | 0.7 | 0.7 | 0.5 |
| Standard | 0.187083 | 0.1 | 0.1 | 0.122474 | 0.122474 | 0.158114 |
| Saline (l.p.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |
| 4 | 0 | 0 | 0 | 0 | 0 | 0 |
| 5 | 0 | 0 | 0 | 0 | 0 | 0 |
| Mean | 0 | 0 | 0 | 0 | 0 | 0 |
| Standard | 0 | 0 | 0 | 0 | 0 | 0 |
| Saline (s.c.) | | | | | | |
| 1 | 0 | 0 | 0 | 0 | 0 | 0 |
| 2 | 0 | 0 | 0 | 0 | 0 | 0 |
| 3 | 0 | 0 | 0 | 0 | 0 | 0 |

TABLE 13-continued

| | Oedema Days after treatment | | | | | |
|---|---|---|---|---|---|---|
| Mouse | 6 | 7 | 9 | 12 | 13 | 14 |
| 4 | 0 | 0 | 0 | 0 | 0 | 0 |
| 5 | 0 | 0 | 0 | 0 | 0 | 0 |
| 6 | 0 | 0 | 0 | 0 | 0 | 0 |
| Mean | 0 | 0 | 0 | 0 | 0 | 0 |
| Standard | 0 | 0 | 0 | 0 | 0 | 0 |

EXAMPLE

Subcutaneous Administration of Amifostine Stimulated Bone Marrow Cell Growth in Humans Subcutaneous Administration of Amifostine in MDS Patients All patients in the study had MDS and were diagnosed as having one of the following subtypes: refractory anemia, refractory anemia with ring sideroblasts, refractory anemia with excess blasts or refractory anemia with excess blasts in transformation. In addition, the patients had thrombocytopenia (platelets <100,000/μl), neutropenia (ANC or absolute neutrophil count<1500/μl) or a hemoglobin untransfused <10 g/dl and/or were transfusion-dependent as defined by requiring at least 4 units of RBC in the 10 weeks prior to entry. They had not received any previous treatment other than transfusion for-MDS within 30 days prior to the study.

A 500 mg vial of amifostine was dissolved in 2.5 ml of 0.9% NaCl for s.c. administration. If the calculated dose of amifostine required more than 2 ml volume for dissolution, a total volume was evenly divided and administered as two s.c. injections. Blood pressure was monitored before treatment and after the first dose at 30 minute intervals for up to 90 minutes. A single dose of amifostine was given at 500 mg. At least three patients were treated with each dose. For one cycle of treatment, the patients were given amifostine once/day Mondays through Fridays for three weeks, followed by two weeks of rest. Hematologic responses to treatment were evaluated by measuring neutrophil count (ANC), platelet count, erythroid response including hemoglobin levels and reticulocyte count, and in vitro colony formation.

Results

Among the patients who received s.c. administration of amifostine, 17 patients were evaluated for hematologic responses. Among the 17 evaluated patients, 4 previously received amifostine intravenously prior to the study. The patients had diverse cytogenetic patterns with 8 patients showing normal karyotype and 9 patients showing abnormal karyotype. Minimal adverse effects were observed in the treated patients: nausea (grade I/II) in one patient, fatigue (grade I/II) in four patients, rash (grade I/II) in six patients, vomiting (grade I/II) in one patient, local reaction (grade III) in one patient and metallic taste (grade I/II) in one patient.

Table 14 shows that 29% of the treated patients showed 50% or greater increase of ANC as compared to pretreatment levels. In addition, 33% of the patients showed 50% or greater increase of platelets as compared to pretreatment levels. Moreover, 71% of the patients showed 50% or greater increase in reticulocyte count as compared to pretreatment levels.

TABLE 14

| | Evaluable | Responders | [Magnitude] |
|---|---|---|---|
| ANC ≧50% ↑ | 17 | 5 (29%) | [330-105 / μl] |
| ANC < 1000 | 8 | 3 (38.5%) | |
| ANC > 1000 | 9 | 2 (22%) | |
| Platelets ≧ 50% ↑ | 9 | 3 (33%) | [23–32,000/ μl] |
| >50,000/ μl | 3 | 3 (100%) | |
| <50,000/ μl | 6 | 0 | |
| Retic count ≧ 50% ↑ | 14 | 10 (71%) | [0.4%–4.8%] |
| RBC Transfusion (≦50% ↓) | 13 | 0 | |
| BM Blasts ↑ (RAEB) | 5 | 2 (RAEB-t, AML) | |
| Hemoglobin >1.5 g/dl ↑ | 7 | 1 | |
| Ring Sideroblast | 7 | 3 ↓ [47%–100%] | |

Figure 7C:
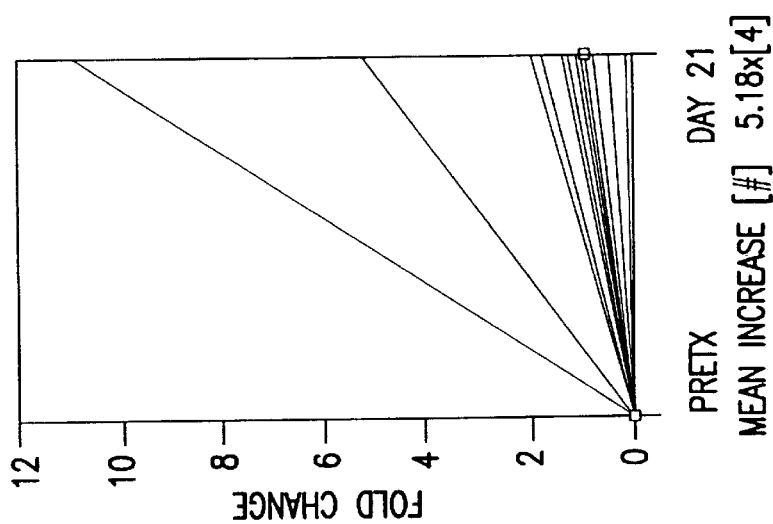
FIG. 7A–7C are three graphs of colony formation by bone marrow progenitor cells obtained from MDS patients after receiving amifostine subcutaneously.
Figure 7B:
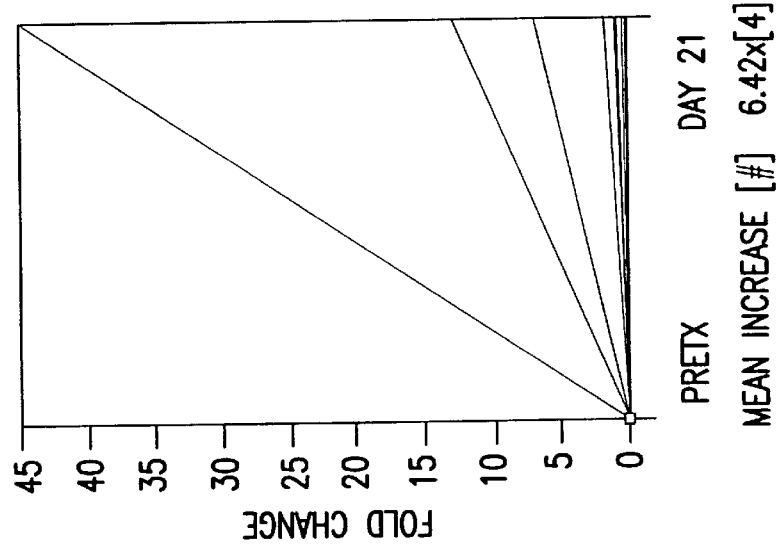
Figure 7A:
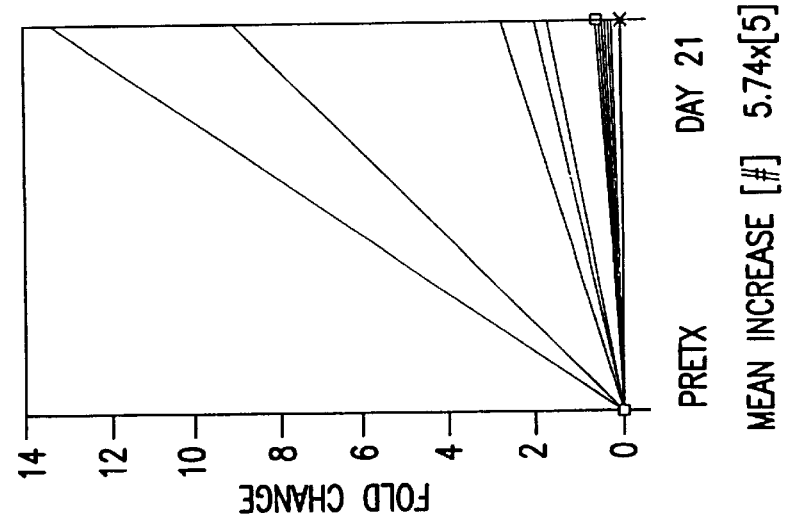

Bone marrow progenitor cells were recovered from the treated patients and assayed for their ability to form CFU-GEMM, BFU-E and CFU-GM colonies in standard methylcellulose assays. FIG. 7A–7C shows that cells obtained from a number of the patients produced bone marrow colonies. These results indicate that subcutaneous administration of amifostine in MDS patients was effective in inducing bone marrow cell growth.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entireties for all purposes.

What is claimed is:

1. A method of treating or protecting a subject against the toxicities associated with the administration of one or more chemotherapeutic agents selected from the group consisting of alkylating agents, platinum agents, anthracyclines, taxanes, and mixtures thereof comprising:

administering to a subject in need thereof a therapeutically effective amount of a compound having the formula:

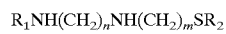

or a pharmaceutically acceptable salt or hydrate thereof, wherein:

$R_1$ is hydrogen, $C_6$–$C_7$ aryl, $C_2$–$C_7$ acyl, or alkyl;
$R_2$ is hydrogen or $PO_3H_2$;
n is an integer from 2 to 6; and
m is an integer from 2 to 6;

in a manner so as to obtain a pharmacokinetic profile wherein the plasma or whole blood concentration of said administered compound, an active metabolite thereof, or both increases at a rate of about 0.1 μM/min. to about 40 μM/min., reaching a maximum concentration about 5 min. to about 60 min. after said administration.

2. The method of claim 1, wherein said one or more chemotherapeutic agents is selected from the group consisting of cyclophosphamide, cisplatin, vinblastine, carboplatin, paclitaxel, and mixtures thereof.

3. The method according to claim 1, wherein said compound is
S-2-(3-aminopropyl)ethyl dihydrogen phosphorothioate (amifostine),
2-(3-aminopropylamino) ethanethiol, S-3-(3-methylaminopropylamino) propane thiol or
S-3-(3-methylaminopropylamino) propyl dihydrogen phosphorothioate.

4. The method of claim 1, wherein said compound is not administered to said subject intravenously or intraperitoneally.

5. The method according to claim 1, wherein said maximum concentration plateaus for a period of about 10 min. to about 130 min.

6. The method according to claim 1, wherein said maximum concentration is reached about 12 min. to about 18 min. following administration.

7. The method according to 1, wherein said maximum is about 1 μM to about 40 μM.

8. The method according to claim 1, wherein $R_1$ is hydrogen or methyl; $R_2$ is hydrogen or $PO_3H_2$; m is 2 or 3; and n is 3.

9. The method of claim 1, wherein said administration is made about 20 to about 90 minutes prior to the administration of the one or more chemotherapeutic agents.

10. The method of claim 1, wherein said compound is S-2-(3-aminopropyl)ethyl dihydrogen phosphorothioate (amifostine).

11. A method of treating or protecting a subject against the toxicities associated with the administration of one or more chemotherapeutic agents selected from the group consisting of alkylating agents, platinum agents, anthracyclines, taxanes, and mixtures thereof comprising:

subcutaneously administering to a subject in need thereof a therapeutically effective amount of a compound having the formula:

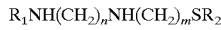

or a pharmaceutically acceptable salt or hydrate thereof, wherein:

$R_1$ is hydrogen, $C_6$–$C_7$ aryl, $C_2$–$C_7$ acyl, or $C_1$–$C_7$ alkyl;
$R_2$ is hydrogen or $PO_3H_2$;

n is an integer from 2 to 6; and
m is an integer from 2 to 6.

12. The method of claim 11, wherein said one or more chemotherapeutic agents comprise one or more of cyclophosphamide, cisplatin, vinblastine, carboplatin, and paclitaxel.

13. The method of claim 11, wherein said subcutaneously administered compound exhibits improved therapeutic efficacy.

14. The method according to claim 11, wherein said compound is
S-2-(3-aminopropyl)ethyl dihydrogen phosphorothioate (amifostine),
2-(3-aminopropylamino) ethanethiol, S-3-(3-methylaminopropylamino) propane thiol or
S-3-(3-methylaminopropylamino) propyl dihydrogen phosphorothioate.

15. The method according to claim 11, wherein said maximum concentration plateaus for a period of about 10 min. to about 130 min.

16. The method according to claim 11, wherein said maximum concentration is reached about 12 min. to about 18 min. following administration.

17. The method according to claim 11, wherein said maximum is about 1 μM to about 40 μM.

18. The method according to claim 11, wherein $R_1$ is hydrogen or methyl; $R_2$ is hydrogen or $PO_3H_2$; m is 2 or 3; and n is 3.

19. The method of claim 11, wherein said administration is made about 20 to about 90 minutes prior to the administration of the one or more chemotherapeutic agents.

20. The method of claim 11, wherein said compound is S-2-(3-aminopropyl)ethyl dihydrogen phosphorothioate (amifostine).

21. A method of protecting normal tissue in cancer patients receiving radiation therapy comprising administering to a cancer patient in need thereof a therapeutically effective amount of S-2-(3-aminopropyl)ethyl dihydrogen phosphorothioate (amofostine) in a manner so as to obtain a pharmacokinetic profile wherein the plasma or whole blood concentration of said administered compound, an active metabolite thereof, or both increases at a rate of about 0.1 μM/min. to about 40 μM/min., reaching a maximum concentration about 5 min. to about 60 min. after said administration.

22. A method of protecting normal tissue in cancer patents receiving radiation therapy comprising subcutaneously administering to a cancer patient in need thereof a therapeutically effective amount of S-2-(3-aminopropyl)ethyl dihydrogen phosphorothioate (amofostine).

* * * * *

UNITED STATES PATENT AND TRADEMARK OFFICE
CERTIFICATE OF CORRECTION

PATENT NO. : 6,218,377 B1
DATED : April 17, 2001
INVENTOR(S) : Martin Stogniew and Philip S. Schein It is certified that error appears in the above-identified patent and that said Letters Patent is hereby corrected as shown below:

Column 6,
Lines 36-37, replace "S-2-(3-aminopropyl)ethyl dihydrogen phosphorothioate" with
-- S-2-(3-aminopropylamino)ethyl dihydrogen phosphorothioate --.
Line 37, replace "$N_2H(CH_2)_3NH(CH_2)_2SPO_3H_2$" with
-- $H_2N(CH_2)_3NH(CH_2)_2SPO_3H_2$ --.
Lines 39-40, replace "$N_2H(CH_2)_3NH(CH_2)_2SH$" with
-- $H_2N(CH_2)_3NH(CH_2)_2SH$ --.

Column 37,
Line 12, replace "S-2-(3-aminopropyl)ethyl dihydrogen phosphorothioate" with
-- S-2-(3-aminopropylamino)ethyl dihydrogen phosphorothioate --.
Line 36, replace "S-2-(3-aminopropyl)ethyl dihydrogen phosphorothioate" with
-- S-2-(3-aminopropylamino)ethyl dihydrogen phosphorothioate --.

Column 38,
Line 12, replace "S-2-(3-aminopropyl)ethyl dihydrogen phosphorothioate" with
-- S-2-(3-aminopropylamino)ethyl dihydrogen phosphorothioate --.
Lime 33, replace "S-2-(3-aminopropyl)ethyl dihydrogen phosphorothioate" with
-- S-2-(3-aminopropylamino)ethyl dihydrogen phosphorothioate --.
Lines 37-38, replace "S-2-(3-aminopropyl)ethyl dihydrogen phosphorothioate" with
-- S-2-(3-aminopropylamino)ethyl dihydrogen phosphorothioate --.
Lines 49-50, replace "S-2-(3-aminopropyl)ethyl dihydrogen phosphorothioate" with
-- S-2-(3-aminopropylamino)ethyl dihydrogen phosphorothioate --.

Signed and Sealed this

Twenty-sixth Day of November, 2002

Attest:

JAMES E. ROGAN
Attesting Officer          Director of the United States Patent and Trademark Office